United States Patent
Kraus

(10) Patent No.: US 9,011,844 B2
(45) Date of Patent: *Apr. 21, 2015

(54) HUMAN CYSTATHIONINE β-SYNTHASE VARIANTS AND METHODS OF PRODUCTION THEREOF

(71) Applicant: The Regents of the University of Colorado, a Body Corporate, Denver, CO (US)

(72) Inventor: Jan P. Kraus, Littleton, CO (US)

(73) Assignee: The Regents of the University of Colorado, a Body Corporate, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 13/826,024

(22) Filed: Mar. 14, 2013

(65) Prior Publication Data

US 2014/0023630 A1 Jan. 23, 2014

Related U.S. Application Data

(62) Division of application No. 13/221,379, filed on Aug. 30, 2011, now Pat. No. 8,398,989, which is a division of application No. 12/359,287, filed on Jan. 24, 2009, now Pat. No. 8,007,787, which is a division of application No. 10/464,811, filed on Jun. 17, 2003, now Pat. No. 7,485,307.

(60) Provisional application No. 60/389,541, filed on Jun. 17, 2002.

(51) Int. Cl.
C12N 9/88 (2006.01)

(52) U.S. Cl.
CPC .................................. *C12N 9/88* (2013.01)

(58) Field of Classification Search
CPC .................................. C12N 9/88; C12N 9/10
USPC .................................................. 435/193, 232
See application file for complete search history.

(56) References Cited

U.S. PATENT DOCUMENTS

| | | | |
|---|---|---|---|
| 5,523,225 A | 6/1996 | Kraus | |
| 5,635,375 A | 6/1997 | Kraus | |
| 5,656,425 A | 8/1997 | Kraus | |
| 6,174,696 B1 | 1/2001 | Seman | |
| 6,436,658 B1 | 8/2002 | Seman | |
| 6,596,701 B1 | 7/2003 | Schwartz et al. | |
| 7,485,307 B2 | 2/2009 | Kraus | |
| 2003/0091543 A1 | 5/2003 | Klein | |
| 2004/0033219 A1 | 2/2004 | Kraus et al. | |
| 2006/0251641 A1 | 11/2006 | Keimel | |
| 2007/0010492 A1 | 1/2007 | Generale | |

FOREIGN PATENT DOCUMENTS

| | | |
|---|---|---|
| CN | 101322840 | 12/2008 |
| EP | 1396537 | 3/2004 |
| WO | 9507714 | 3/1995 |
| WO | 0102600 | 1/2001 |

OTHER PUBLICATIONS

Sequence alignment between SEQ ID No. 2 and AC P35520 (1994). Reference embedded in the Office Action.*
Kery et al. (Arch. Biochem. Biophys. 355, 222-232, 1998).*
(Janosik et al., Februrary 2001, Acta Crystallogr. D Biol. Crystallogr. 57(Pt 2), 289-291).*
Alexander et al., 1994, "Evolutionary relationships among pyridoxal-5'-phosphate-dependent enzymes. Regio-specific alpha, beta and gamma families." Eur. J. Biochem. 219(3), 953-60.
Amersham Pharmacia Biotech (1997), "A novel protease for site-specific cleavage of GST fusion proteins," Science Tools, 2(2), 26.
Bateman, 1997, "The structure of a domain common to archaebacteria and the homocystinuria disease protein." Trends Biochem. Sci. 22, 12-13.
Bruno et al., 2001, "Functional properties of the active core of human cystathione beta-synthase crystals." J. Biol. Chem. 276(1), 16-19.
Bukovska et al., 1994, "Expression of human cystathionine beta-synthase in *Escherichia coli*: purification and characterization." Protein Expr. Purif. 5, 442-8.
Byrne et al., 1988, "DNA sequences of the cysK regions of *Salmonella typhimurium* and *Escherichia coli* and linkage of the cysK regions to ptsH." J. Bacteriol. 170(7), 3150-7.
Finkelstein et al., 1975, "Activation of cystathionine synthase by adenosylmethionine and adenosylethionine." Biochem. Biophys. Res. Commun. 66, 81-87.
Finkelstein et al., 1984, "Inactivation of betaine-homocysteine methyltransferase by adenosylmethionine and adenosylethionine." Biochem Biophys Res Commun 118(1), 14-9.
Finkelstein and Martin, "Methionine metabolism in mammals. Distribution of homocysteine between competing pathways." 1984, J. Biol. Chem. 259(15), 9508-13.
Gallagher et al., 1998, "Structure and control of pyridoxal phosphate dependent allosteric threonine deaminase." Structure 6(4), 465-75.
Janosik et al., 2001, Crystallization and preliminary X-ray diffraction analysis of the active core of human recombinant cystathione beta-synthase: an enzyme involved in vascular disease, Acta Crystallogr. D Biol. Crystallogr. 57(Pt 2), 289-291.
Janosik et al., 2001, "Impaired heme binding and aggregation of mutant cystathionine beta-synthase subunits in homocystinuria." Am. J. Hum. Genet. 68(6), 1506-13.
Janosik et al., 2001, "Regulation of human cystathionine beta-synthase by S-adenosyl-L-methionine: evidence for two catalytically active conformations involving an autoinhibitory domain in the C-terminal region." Biochemistry 40(35), 10625-33.

(Continued)

*Primary Examiner* — Tekchand Saidha
(74) *Attorney, Agent, or Firm* — McDonnell Boehnen Hulbert & Berghoff LLP

(57) ABSTRACT

Human cystathionine β-synthase variants are disclosed, as well as a method to produce recombinant human cystathionine β-synthase and variants thereof. More particularly, the role of both the N-terminal and C-terminal regions of human CBS has been studied, and a variety of truncation mutants and modified CBS homologs are described. In addition, a method to express and purify recombinant human cystathionine β-synthase (CBS) and variants thereof which have only one or two additional amino acid residues at the N-terminus are described.

14 Claims, 6 Drawing Sheets

(56) References Cited

OTHER PUBLICATIONS

Jhee et al., 2000, "Yeast cystathionine beta-synthase is a pyridoxal phosphate enzyme but, unlike the human enzyme, is not a heme protein." J. Biol. Chem. 275(16), 11541-4.

Jhee et al., 2000, "Domain architecture of the heme-independent yeast cystathionine beta-synthase provides insights into mechanisms of catalysis and regulation." Biochemistry 39(34), 10548-56.

Kabil and Banerjee, "Deletion of the regulatory domain in the pyridoxal phosphate-dependent heme protein cystathionine beta-synthase alleviates the defect observed in a catalytic site mutant." 1999, J. Biol. Chem. 274(44), 31256-60.

Kery et al., 1994, "Transsulfuration depends on heme in addition to pyridoxal 5'-phosphate. Cystathionine beta-synthase is a heme protein." J. Biol. Chem. 269, 25283-25288.

Kery, 1995, "Delta-aminolevulinate increases heme saturation and yield of human cystathionine beta-synthase expressed in *Escherichia coli*." Arch. Biochem. Biophys. 316, 24-29.

Kery et al., 1998, "Trypsin cleavage of human cystathionine beta-synthase into an evolutionarily conserved active core: structural and functional consequences." Arch. Biochem. Biophys. 355, 222-232.

Kery et al., 1999, "Binding of pyridoxal 5'-phosphate to the heme protein human cystathionine beta-synthase." Biochemistry 38(9), 2716-24.

Kluijtmans et al., 1996, "Defective cystathionine beta-synthase regulation by S-adenosylmethionine in a partially pyridoxine responsive homocystinuria patient." J. Clin. Invest 98, 285-289.

Kozich et al., 1992, "Screening for mutations by expressing patient cDNA segments in *E. coli*: homocystinuria due to cystathionine beta-synthase deficiency." Hum. Mutation 1, 113-123.

Kraus et al., 1983, "Cystathionine beta-synthase from human liver: improved purification scheme and additional characterization of the enzyme in crude and pure form." Arch. Biochem. Biophys. 222, 44-52.

Kraus, 1987, "Cystathionine beta-synthase (human)." Methods Enzymol. 143, 388-394.

Kutzbach et al., 1967, "Feedback inhibition of methylenetetrahydrofolate reductase in rat liver by S-adenosylmethionine." Biochim. Biophys. Acta 139, 217-220.

Kutzbach et al., 1971, "Mammalian methylenetetrahydrofolate reductase. Partial purification, properties, and inhibition by S-adenosylmethionine." Biochim. Biophys. Acta 250, 459-477.

Maclean et al., 2000, "Transsulfuration in *Saccharomyces cerevisiae* is not dependent on heme: purification and characterization of recombinant yeast cystathionine beta-synthase." J. Inorg. Biochem. 81(3), 161-71.

Maclean et al., 2002, "High homocysteine and thrombosis without connective tissue disorders are associated with a novel class of cystathionine beta-synthase (CBS) mutations." Hum. Mutat. 19(6), 641-55.

Meier et al., 2001, "Structure of human cystathionine beta-synthase: a unique pyridoxal 5'-phosphate-dependent heme protein." EMBO J. 20(15), 3910-6.

Mudd et al., 2001, "Disorders of transsulfuration," in The Metabolic and Molecular Bases of Inherited Disease, 8 Ed. (Stanbury et al., eds.), McGraw-Hill, New York, pp. 2007-2056.

Nozaki et al., 2001, "Characterization of transsulfuration and cysteine biosynthetic pathways in the protozoan hemoflagellate, *Trypanosoma cruzi*. Isolation and molecular characterization of cystathionine beta-synthase and serine acetyltransferase from *Trypanosoma*." J. Biol. Chem. 276(9), 6516-23.

Ojha et al., 2002, "Effects of heme ligand mutations including a pathogenic variant, H65R, on the properties of human cystathionine beta-synthase." Biochemistry 41(14), 4649-54.

Rolland et al., 1993, "O-acetylserine(thiol)lyase from spinach (*Spinacia oleracea* L.) leaf: cDNA cloning, characterization, and overexpression in *Escherichia coli* of the chloroplast isoform." Arch. Biochem. Biophys. 300(1), 213-22.

Roper et al., 1992, "Rat cystathionine beta-synthase: expression of four alternatively spliced isoforms in transfected cultured cells." Arch. Biochem. Biophys. 298, 514-521.

Salzmann et al., 2000, "Rates of evolution of pyridoxal-5'-phosphate-dependent enzymes." Biochem. Biophys. Res. Commun. 270(2), 576-80.

Shan et al., 1998, "Correction of disease-causing CBS mutation in yeast." Nat. Genet. 19, 91-93.

Shan et al., 2001, "Mutations in the regulatory domain of cystathionine beta synthase can functionally suppress patient-derived mutations in cis." Hum. Mol. Genet. 10(6), 635-643.

Taoka et al., 1998, "Evidence for heme-mediated redox regulation of human cystathionine beta-synthase activity." J. Biol. Chem. 273, 25179-25184.

Taoka et al., 1999, "Assignment of enzymatic functions to specific regions of the PLP-dependent heme protein cystathionine beta-synthase." Biochemistry 38(40), 13155-61.

Taoka and Banerjee, 2001, "Characterization of NO binding to human cystathionine beta-synthase: possible implications of the effects of CO and NO binding to the human enzyme." J. Inorg. Biochem. 87(4), 245-51.

Taoka and Banerjee, 2002, "Stopped-flow kinetic analysis of the reaction catalyzed by the full-length yeast cystathionine beta-synthase." J. Biol. Chem. 277(25): 22421-5.

Zhang et al., 1999, "Characteristics and crystal structure of bacterial inosine-5'-monophosphate dehydrogenase." Biochemistry 38(15), 4691-700.

Banerjee and Zou, 2005, "Redox regulation and reaction mechanism of human cystathionine-beta-synthase: a PLP-dependent hemesensor protein." Arch Biochem Biophys 433(1): 144-56.

Carballal et al., 2008, "Dioxygen reactivity and heme redox potential of truncated human cystathionine beta-synthase." Biochemistry 47(10): 3194-201.

Cherney et al., 2007, "Ferrous human cystathionine beta-synthase loses activity during enzyme assay due to a ligand switch process." Biochemistry 46(45): 13199-210.

Dong et al., 1997, "Secondary Structure of Recombinant Human Cystathionine beta-Synthase in Aqueous Solution: Effect of Ligand Binding and Proteolytic Truncation." Arch. Biochem. Biophys. 344(1): 125-32.

Frank et al., 2008, "Purification and characterization of the wild type and truncated human cystathionine beta-synthase enzymes expressed in *E. coli*." Arch Biochem Biophys 470(1): 64-72.

Jhee and Kruger, 2005, "The role of cystathionine beta-synthase in homocysteine metabolism." Antioxid Redox Signal. 7(5-6): 813-22.

Kraus et al., 1993, "Human cystathionine beta-synthase cDNA: sequence, alternative splicing and expression in cultured cells." Hum Mol Genet. 2(10): 1633-8.

Lodha et al., 2009, "Investigation of residues Lys112, Glu136, His138, Gly247, Tyr248, and Asp249 in the active site of yeast cystathionine beta-synthase." Biochem Cell Biol. 87(3): 531-40.

Park et al., 2006, "Recombinant adeno-associated virus mediated gene transfer in a mouse model for homocystinuria." Exp Mol Med. 38(6): 652-61.

Sen et al., 2007, "Cystathionine-beta-synthase gene transfer and 3-deazaadenosine ameliorate inflammatory response in endothelial cells." Am J Physiol Cell Physiol. 293(6): C1779-87.

Singh et al., 2009, "Modulation of the heme electronic structure and cystathionine beta-synthase activity by second coordination sphere ligands: The role of heme ligand switching in redox regulation." J Inorg Biochem. 103(5): 689-97.

Singh and Kruger, 2009, "Functional rescue of mutant human cystathionine beta-synthase by manipulation of Hsp26 and Hsp70 levels in *Saccharomyces*." J. Biol. Chem. 284(7): 4238-45.

Van Guldener and Stehouwer, 2001, "Homocysteine-lowering treatment: an overview." Expert Opin Pharmacother. 2(9): 1449-60.

Wang et al., 2005, "Expression of mutant human cystathionine beta-synthase rescues neonatal lethality but not homocystinuria in a mouse model." Hum Mol Genet. 14(15): 2201-8.

Yamanishi et al., 2006, "Structural insights into pathogenic mutations in heme-dependent cystathionine-betasynthase." J Inorg Biochem 100(12): 1988-95.

Yap, 2003, "Classical homocystinuria: vascular risk and its prevention." J Inherit Metab Dis. 26(2-3): 259-65.

(56) References Cited

OTHER PUBLICATIONS

Zou and Banerjee, 2003, "Tumor Necrosis Factor-alpha-induced Targeted Proteolysis of Cystathionine beta-Synthase Modulates Redox Homeostasis." J. Biol. Chem. 278(19): 16802-8.

Amersham Pharmacia Biotech, Saluta and Bell (1998), "Troubleshooting GST fusion protein expression in E. coli." Life Science News 1: 1-3.

Taoka et al., 1999, "Characterization of the Heme and Pyridoxal Phosphate Cofactors of Human Cystathionine beta-Synthase Reveals Nonequivalent Active Sites." Biochemistry 38: 2738-2744.

\* cited by examiner

FIG. 5

```
CBS_HS    MPSETPQAEVGPTGCPHRSGPHSAKGSLEKGSPEDKEAKEPLWIRPDAPSRCTWQLGRPA  60
CBS_DM    -------------------------------MPQPKPYERPADFIDPGKPSKCKWHLG-TA  29
CBS_DD    ----------------------------------------MSAPEGPSKCTWTPN-TT  17
CBS_SC    ------------------------------------------------------------
OASS_TA   ------------------------------------------------------------
OASS_ST   ------------------------------------------------------------

CBS_HS    SESPHHHTAPAKSPKILPDILKKIGDTPMVRINKIGKKFGLKCELLAKCEFFNAGGSVKD  120
CBS_DM    EKSPHIHRGIAHRQQITPNILEVIGCTPLVKLNNIPASDGIECEMYAKCEFLNPGGSVKD  89
CBS_DD    ENTPHTTRRTPKK-LIMDNILDNIGGTPLVRVNKVSS--DLECELVAKCEFFNAGGSVKD  74
CBS_SC    -------MTKSEQQADSRHNVIDLVGNTPLIALKKLPKALGIKPQIYAKLELYNPGGSIKD  54
OASS_TA   ---------MGEASSPAIAKDVTELIGNTPLVYLNKVTDG--CVGRVAAKLESMEPCSSVKD  51
OASS_ST   -------------SKIYEDNSLTIGHTPLVRLNRIGN-----GRILAKVESRNPSFSVKC  43

CBS_HS    RIS123  . . .  363ELQEGQRCVVILPDSVRNYMTKFLSDRWMLQKGFLKEEDLTEKKP  407
CBS_DM    RIG92   . . .  332KLKKGQRCVVILPDGIRNYMTKFVSDNWMEARNFK--EPVNEHGH  374
CBS_DD    RIG77   . . .  316QLKKGQRCVVLLADSIRNYMTKHLNDDWLVDNGFVDPEYKTKDQQ  360
CBS_SC    RIA57   . . .  306ELTEDDVIVAIFPDSIRSYLTKFVDDEWLKKNNLWDDDVLARFDS  350
OASS_TA   RIG54   . . .  288PENAGKLFVVVFPSFGERYLSSVLFHSIKKEAESMVVE-------  325
OASS_ST   RIG46   . . .  298ESFTNKNIVVILPSSGERYLSTALFADLFTEKELQQ--------  323

CBS1
CBS_HS    ---------------WWWHLRVQELGLSAPLTVLP-TTICGHTIETLREKGFDQAPVVD-EAG  453
CBS_DM    ---------------WWWSLAIAELELPAPPVILKSDATVGEAIALMKKHRVDQLEVVDQDDG  422
CBS_DD    E---------EEKYHGATVKDLTLPKPITISA-TTTCAAVQLLQYGFDQLPVVSESKI  410
CBS_SC    SKLEASTTKYADVFGNATVKDLHL-KPVVSVKETAKVTDVIKILKDNGFDQLEVLT-EDG  408
OASS_TA   ------------------------------------------------------------
OASS_ST   ------------------------------------------------------------

CBS_HS    VILGMVTLGNMLSSLLAGKVQPSDQVG------KVIY-------------KQFKQIRL  492
CBS_DM    SVLGVVGQETLITQIVSMNRQQSDPAI------KALN-------------KRVIRLNE  461
CBS_DD    VLVNSLLVTSLT--YASKFAVPTDAVS------KVMFRF----------TKNEKYIPITQ  452
CBS_SC    KLSGLVTLSELLRKLSINNSNNDNTIKGKYLDFKKLNNFNDVSSYNENKSGKKKFIKFDE  468
OASS_TA   ------------------------------------------------------------
OASS_ST   ------------------------------------------------------------

CBS2
CBS_HS    TDTLGRLSHTLEMDHFALVVHEQIQTHSTGKSSQRQMVFGVVTAIDLLNFVAAQERDQK-  551
CBS_DM    SEILGKLARVLEVDPSVLILGK----NPAGKVELK----ALATKLDVTTFIAAGKQKPKA  513
CBS_DD    STSLATLSKFFENHSSAIVTEN---------DEIIS-----IVTKIDLLTYLMKSQQKN--  497
CBS_SC    NSKLSDLNREPEKNSSAVTTDG---------LKPIH-----IVTKMDLLSYLA--------  507
OASS_TA   ------------------------------------------------------------
OASS_ST   ------------------------------------------------------------

CBS_HS    ----------                  (1-123 and 363-551 of SEQ ID NO:2)
CBS_DM    NGTTNGGSH 522               (1-92 and 332-522 of SEQ ID NO:18)
CBS_DD    ----------                  (1-77 and 316-479 of SEQ ID NO:19)
CBS_SC    ----------                  (1-57 and 306-507 of SEQ ID NO:20)
OASS_TA   ----------                  (1-54 and 288-325 of SEQ ID NO:21)
OASS_ST   ----------                  (2-46 and 288-323 of SEQ ID NO:22)
```

HUMAN CYSTATHIONINE β-SYNTHASE VARIANTS AND METHODS OF PRODUCTION THEREOF

CROSS-REFERENCE TO RELATED APPLICATIONS

This application is a divisional of U.S. patent application Ser. No. 13/221,379, filed Aug. 30, 2011, now U.S. Pat. No. 8,398,989, issued Mar. 19, 2013, which is a divisional of U.S. patent application Ser. No. 12/359,287, filed Jan. 24, 2009, now U.S. Pat. No. 8,007,787, granted Aug. 30, 2011, which is a divisional of U.S. patent application Ser. No. 10/464,811, filed Jun. 17, 2003, now U.S. Pat. No. 7,485,307, granted Feb. 3, 2009, which claims priority under 35 U.S.C. 119(e) from U.S. Provisional Application Ser. No. 60/389,541, filed Jun. 17, 2002. The entire disclosure of U.S. patent application Ser. No. 13/221,379, U.S. patent application Ser. No. 12/359,287, U.S. patent application Ser. No. 10/464,811 and U.S. Provisional Application Ser. No. 60/389,541 is incorporated herein by reference.

GOVERNMENT RIGHTS

This invention was supported in part with funding provided by NIH Grant Nos. P01HD0805 and HL65217, each awarded by the National Institutes of Health. The government may have certain rights to this invention.

FIELD OF THE INVENTION

The present invention generally relates to modified forms of cystathionine β-synthase, including homologues that have catalytic activity but a reduced or lack of ability to bind heme. The present invention also relates to a method to produce recombinant cystathionine β-synthases, including homologues thereof.

BACKGROUND OF THE INVENTION

Cystathionine β-synthase (CBS) plays an essential role in homocysteine metabolism in eukaryotes (Mudd et al., 2001, in *The Metabolic and Molecular*, Bases of Inherited Disease, 8 Ed., pp. 2007-2056, McGraw-Hill, New York). The CBS enzyme catalyzes a pyridoxal 5'-phosphate (PLP)-dependent condensation of serine and homocysteine to form cystathionine, which is then used to produce cysteine by another PLP-dependent enzyme, cystathionine γ-lyase. In mammalian cells that possess the transsulfuration pathway, CBS occupies a key regulatory position between the remethylation of Hcy to methionine or its alternative use in the biosynthesis of cysteine. The relative flux between these two competing pathways is roughly equal and is controlled by intracellular S-adenosylmethionine (AdoMet) concentrations (Finkelstein and Martin, 1984, *J. Biol. Chem.* 259(15), 9508-13). AdoMet activates the mammalian CBS enzyme by as much as 5-fold with an apparent dissociation constant of 15 µM (Finkelstein et al., 1975, *Biochem. Biophys. Res. Commun.* 66, 81-87; Roper et al., 1992, *Arch. Biochem. Biophys.* 298, 514-521; Kozich et al., 1992, *Hum. Mutation* 1, 113-123). Conversely, the same compound acts as an allosteric inhibitor of homocysteine remethylation by inhibiting 5,10-methylenetetrahydrofolate reductase (Kutzbach et al., 1967, *Biochim. Biophys. Acta* 139, 217-220; Kutzbach et al., 1971, *Biochim. Biophys. Acta* 250, 459-477) and betaine-homocysteine methyltransferase (Finkelstein et al., 1984, *Biochem Biophys Res Commun* 118(1), 14-9). Deficiency of CBS is the most common cause of inherited homocystinuria, a serious life threatening disease that results in severely elevated homocysteine levels in plasma, tissues and urine. Symptoms include dislocated optic lenses, skeletal disorders, mental retardation and premature arteriosclerosis and thrombosis (Mudd et al., 2001, supra).

Human CBS is a member of a large family of PLP-dependent enzymes that operate almost exclusively in the metabolism of amino acids. Members of this family are of multiple evolutionary origins (Salzmann et al., 2000, *Biochem. Biophys. Res. Commun.* 270(2), 576-80), but can be classified into four distinct families depending on their folds: the large α family, the β family, the D-alanine aminotransferase family, and the alanine racemase family (Alexander et al., 1994, *Eur. J. Biochem.* 219(3), 953-60). CBS belongs to the β family of PLP-dependent enzymes, members of which catalyze replacement and elimination reactions at Cβ.

While the catalytic cores of cysteine synthases (CS) and CBS enzymes exhibit high levels of homology, the N- and the C-terminal non-catalytic regions of these proteins show virtually no similarity. Human CBS (represented herein by SEQ ID NO:2) contains an N-terminal region of ~70 amino acid (FIG. 1), which accommodates the heme prosthetic group (Meier et al., 2001, *Embo J.* 20(15), 3910-6). The function of this ligand is unknown but a number of studies indicate it may play either a regulatory or structural role (Taoka et al., 1998, *J. Biol. Chem.* 273, 25179-25184; Taoka and Banerjee, 2001, *J. Inorg. Biochem.* 87(4), 245-51; Kery et al., 1994, *J. Biol. Chem.* 269, 25283-25288; Kery, 1995, *Arch. Biochem. Biophys.* 316, 24-29). The observation that both yeast (Jhee et al., 2000, *J. Biol. Chem.* 275(16), 11541-4; Maclean et al., 2000, *J. Inorg. Biochem.* 81(3), 161-71; Jhee et al., 2000, *Biochemistry* 39(34), 10548-56) and *Trypanosoma cruzi* (Nozaki et al., 2001, *J. Biol. Chem.* 276(9), 6516-23) CBS lack heme indicates that it is not directly involved in catalysis (Maclean et al., 2000, supra; Jhee et al., 2000, *Biochemistry*, supra).

The C-terminal regulatory domain of human CBS consists of ~140 amino acid residues (Kery et al., 1998, *Arch. Biochem. Biophys.* 355, 222-232). This region is required for tetramerization of the human enzyme and AdoMet activation (Kery et al., 1998, ibid.). The C-terminal regulatory region also encompasses the previously defined "CBS domain" (Bateman, 1997 *Trends Biochem. Sci.* 22, 12-13). This hydrophobic sequence (CBS1), spanning amino acid residues 415-468 of SEQ ID NO:2, is conserved in a wide range of otherwise unrelated proteins. Its function remains unknown, although the sharp transition of thermally induced CBS activation and the observation that mutations in this domain can constitutively activate the enzyme indicates that it plays a role in the autoinhibitory function of the C-terminal region (Janosik et al., 2001, *Biochemistry* 40(35), 10625-33; Shan et al., 2001, *Hum. Mol. Genet.* 10(6), 635-643). Based on sequence similarity with another CBS domain containing protein, inosine 5'-monophosphate dehydrogenase (IMPDH) from *Streptomyces pyogenes*, a second, less conserved CBS domain (CBS2) has recently been identified between amino acid residues 486 to 543 of SEQ ID NO:2 in the C-terminal regulatory region of human CBS (FIG. 1, Shan et al., ibid.). Two well conserved CBS domains are also present in the C-terminal region of the yeast CBS, which is of approximately the same length as the human enzyme (FIG. 1). The yeast enzyme functions as a tetramer, but is not activated by AdoMet (Jhee et al., 2000, *J. Biol. Chem.* 275(16), 11541-4). CBS from *T. cruzi*, which is also unresponsive to AdoMet, lacks the typical CBS C-terminal region and exists predominantly as a tetramer. This observation has lead to speculation that CBS tetramerization is not exclusively a function of the C-terminal region (Nozaki et al., 2001, *J. Biol. Chem.* 276(9), 6516-23).

All of the CS enzymes lack both the N-terminal heme binding domain, and the C-terminal regulatory region (FIG. 1). These enzymes function as dimers, do not bind heme and are not activated by AdoMet (Byrne et al., 1988, *J. Bacteriol.* 170(7), 3150-7; Rolland et al., 1993, *Arch. Biochem. Biophys.* 300(1), 213-22).

Structure/function analyses of products derived from limited trypsinolysis of human CBS provided some initial insight into the domain architecture of this protein (Kery et al., 1998, supra). It was determined that the N-terminal 39 amino acid region does not play a significant role in the native structure of fully-folded CBS as removal of this region by partial tryptic cleavage does not affect AdoMet, PLP, heme binding, or tetramer formation (Kery et al., 1998, ibid.). Further proteolysis leads to the removal of the entire C-terminal regulatory region, yielding a proteolytically resistant core, consisting of amino acid residues 40-413 of SEQ ID NO:2. The removal of the C-terminal domain causes the enzyme to dissociate from tetramers to dimers. This change in oligomeric status of the enzyme is accompanied by an increase in tryptophan fluorescence, possibly caused by exposing a tryptophan cluster at positions 408-410 of SEQ ID NO:2. The truncated protein showed no change in both its UV and visible absorption spectra indicating that it maintains the structural features of full-length CBS and is unaffected in its ability to bind both PLP and heme (Kery et al., 1998, ibid.). The active core forms dimers and is about two to three-fold more active than the full-length tetramer, but cannot be further activated by AdoMet (Kery et al., 1998, ibid.).

Apart from AdoMet, several other modes of CBS activation have been reported. These include partial thermal denaturation (Janosik et al., 2001, supra), limited proteolysis (Kery et al., 1998, supra) and the presence of certain C-terminal mutations (Janosik et al., 2001, supra; Shan et al., 2001, supra). A possible common CBS activation mechanism has been proposed whereby the C-terminal region of CBS acts an autoinhibitory domain and that certain mutations, binding of AdoMet, limited trypsinolysis or partial thermal denaturation all serve to displace this domain from its zone of inhibition (Janosik et al., 2001, supra; Shan et al., 2001, supra).

A recombinant human CBS enzyme similar to the above-described "proteolytically resistant core" (i.e., 40-413 of SEQ ID NO:2) has recently been expressed in *E. coli* and purified to homogeneity (Janosik et al., 2001, *Acta Crystallogr. D Biol. Crystallogr.* 57(Pt 2), 289-291). This truncated enzyme, comprising amino acid residues 1-413 of SEQ ID NO:2, has been crystallized and its X-ray structure determined (Meier et al., 2001, supra). The crystals contained three dimers per asymmetric unit and each dimer contained one heme and one PLP per subunit. It was observed that the heme-binding region of the enzyme is almost completely disordered; the only exception is a short $3_{10}$ helix formed by amino acid residues 60-62 of SEQ ID NO:2. Two N-terminal residues, Cys52 and His65 were identified as thiolate and histidine ligands to the heme. The heme resides in a small hydrophobic pocket at the outer end of each dimer, distant from the PLP cofactor, which is deeply buried in the active site and accessible only via a narrow channel (Meier et al., 2001, supra). The finding that the heme is relatively distant from the PLP and the fact that the heme iron is ligated from both sides by the amino acid residues provided evidence against its direct catalytic involvement (Meier et al., 2001, supra). However, the function of the heme group was still unknown at the time of the present invention.

U.S. Pat. No. 5,523,225 to Kraus, incorporated herein by reference in its entirety, describes the purified and isolated DNA for human cystathionine β-synthase (CBS), as well as restriction fragment length polymorphisms (RFLP) of the CBS gene, standard recombinant vectors comprising such DNA, recombinant host cells that express such DNA, and the protein encoded by the DNA. In this patent, conventional vectors were used to clone and express CBS.

U.S. Pat. No. 5,635,375 to Kraus, incorporated herein by reference in its entirety, describes a method of increasing the yield and heme saturation of cystathionine β-synthase produced by recombinant microorganisms. The method includes conventional expression of recombinant CBS fusion proteins in microorganisms (e.g., conventional expression vectors, production microorganisms and conditions were used), but with the incorporation of a heme precursor, such as δ-aminolevulinate, into the culture medium during the growth of the recombinant microorganisms. The inclusion of the heme precursor resulted in significantly improved CBS activity, yield of the enzyme and heme saturation of the enzyme.

U.S. Pat. No. 5,656,425 to Kraus, incorporated herein by reference in its entirety, describes a rapid screening process for detecting, localizing and expressing pathogenic mutations in the cystathionine β-synthase gene of a patient. The process includes the production of hybrid cDNAs of CBS DNA wherein subregions from the patient cDNA are expressed in the context of an otherwise wild-type CBS construct. The expression products of the hybrids are evaluated for decreased enzyme activity as a marker for pathogenic mutations with the patient cDNA.

To allow for effective and efficient purification of a recombinantly produced protein, it is conventional in the art to express the desired recombinant protein as part of a fusion protein, wherein the fusion partner is typically a protein that can: enhance a protein's stability, provide other desirable biological activity, and/or assist with the purification of a protein (e.g., by affinity chromatography). Fusion partners can be joined to amino and/or carboxyl termini of the recombinant protein to be produced, usually via a linker region to allow for the proper folding of the proteins in the fusion, and are typically susceptible to cleavage by a protease in order to enable straight-forward recovery of the desired recombinant protein. Cleavage of the fusion partner from the desired protein typically results in an extension of a few or several amino acid residues at the N- or C-terminal portion of the desired recombinant protein (depending on where the fusion partner is linked) which are heterologous to the recombinant protein sequence.

With regard to the CBS protein, which is routinely produced as a recombinant fusion protein, all of the publicly described recombinant GSH-CBS proteins described prior to the present invention have included a variable length (e.g., 12-23) of additional non-CBS amino acid residues at the amino terminus of the protein. This is a conventional result in the art, and it has not been discussed as an issue with regard to the production and use of the CBS protein. One of skill in the art can readily produce and purify an apparently functional CBS protein by conventional recombinant expression techniques even with the N-terminal extension artifact of the recombinant expression process. Moreover, as discussed above, previous studies have shown that the N-terminal 39 amino acid region does not play a significant role in the native structure of the fully-folded CBS, as the tryptic cleavage of this domain from the wild type enzyme does not affect AdoMet, PLP, heme binding, or tetramer formation (Kery et al., 1998, *Arch. Biochem. Biophys.* 355, 222-232). However, the present inventors, without being bound by theory, believe that the addition of non-human, non-CBS amino acid residues at the N-terminus of the CBS protein alters the properties of the enzyme. In addition, human CBS is a desirable therapeutic reagent, but the presence of non-human, non-CBS residues at the N-terminus of the recombinant CBS protein may have serious consequences for therapeutic applications, since these residues may elicit the formation of antibodies against the recombinant protein in human patients. Finally, while CBS is an attractive therapeutic molecule, there may be risks associated with administering the full-length protein or a nucleic acid encoding the same to a patient.

Therefore, there is a need in the art for an improved method to produce recombinant cystathionine β-synthase, including isoforms (variants) of the enzyme, that are effective and safe for use in human therapeutic applications.

SUMMARY OF THE INVENTION

One embodiment of the present invention relates to an isolated human cystathionine β-synthase variant. The variant is selected from: (a) a protein consisting essentially of an amino acid spanning from a starting position of one of amino acid residues from about 66-84 of SEQ ID NO:2 to an ending position of one of amino acid residues from about 382-532 or 543-551 of SEQ ID NO:2; and (b) a homologue of the protein of (a), wherein the homologue consists essentially of an amino acid sequence that is at least about 70% identical to the amino acid sequence of (a). The isolated human cystathionine β-synthase variant catalyzes the formation of cystathionine and does not bind heme.

In one aspect, the starting position of the variant is one of amino acid residues from about 66-71 of SEQ ID NO:2. In another aspect, the starting position is one of amino acid residues from about 70-84 of SEQ ID NO:2. In yet another aspect, the starting position is about position 70 or 71 of SEQ ID NO:2.

In one aspect, the ending position is one of amino acid residues from about 382-523 or 543-551 of SEQ ID NO:2. In another aspect, the ending position is one of amino acid residues from about 400-523 or 543-551 of SEQ ID NO:2. In yet another aspect, the ending position is one of amino acid residues from about 413-523 or 543-551 of SEQ ID NO:2. In another aspect, the ending position is one of amino acid residues from about 441-523 or 543-551 of SEQ ID NO:2. In another aspect, the ending position is one of amino acid residues from about 488-523 or 543-551 of SEQ ID NO:2. In another aspect, the ending position is one of amino acid residues from about 496-523 or 543-551 of SEQ ID NO:2. In another aspect, the ending position is one of amino acid residues from about 543-551 of SEQ ID NO:2.

In one aspect, the protein of (a) consists essentially of an amino acid spanning from a starting position of one of amino acid residues from about 66-84 of SEQ ID NO:2 to an ending position of one of amino acid residues from about 400-523 or 543-551 of SEQ ID NO:2. In another aspect, the protein of (a) consists essentially of an amino acid spanning from a starting position of one of amino acid residues from about 70 or 71 of SEQ ID NO:2 to an ending position of one of amino acid residues from about 400-523 or 543-551 of SEQ ID NO:2. In yet another aspect, the protein of (a) consists essentially of an amino acid spanning from a starting position of one of amino acid residues from about 66-84 of SEQ ID NO:2 to an ending position of about 551 of SEQ ID NO:2. In yet another aspect, the protein of (a) consists essentially of an amino acid spanning from a starting position of one of amino acid residues from about 70 or 71 of SEQ ID NO:2 to an ending position of about 400 of SEQ ID NO:2. In yet another aspect, the protein of (a) consists essentially of an amino acid spanning from a starting position of about position 70 or 71 of SEQ ID NO:2 to an ending position of one of amino acid residues from about 544-551 of SEQ ID NO:2. In yet another aspect, the protein of (a) consists essentially of an amino acid spanning from a starting position of about position 70 or 71 of SEQ ID NO:2 to an ending position of about 551 of SEQ ID NO:2.

In one aspect, the homologue is at least about 80% identical to the amino acid sequence of (a), or at least about 90% identical to the amino acid sequence of (a).

Yet another embodiment of the present invention relates to an isolated human cystathionine β-synthase variant consisting essentially of an amino acid sequence that differs from SEQ ID NO:2 by at least a deletion or mutation of Cys52 and His65 of SEQ ID NO:2. Preferably, such a variant catalyzes the formation of cystathionine and does not bind heme. In one aspect, the variant further differs from SEQ ID NO:2 by a deletion of at least amino acid positions 1-39 of SEQ ID NO:2. In another aspect, the variant further differs from SEQ ID NO:2 by a deletion of at least amino acid positions 1-50 of SEQ ID NO:2. In another aspect, the variant further differs from SEQ ID NO:2 by a deletion of at least amino acid positions 1-60 of SEQ ID NO:2. In yet another aspect, the variant further differs from SEQ ID NO:2 by a deletion of at least amino acid positions 1-70 of SEQ ID NO:2. In yet another aspect, the variant further differs from SEQ ID NO:2 by a deletion of between about 1 and about 8 amino acids from the C-terminus of SEQ ID NO:2. In another aspect, the variant further differs from SEQ ID NO:2 by a deletion of between about 19 and about 169 amino acids from the C-terminus of SEQ ID NO:2. In another aspect, the variant further differs from SEQ ID NO:2 by a deletion of between about 28 and about 169 amino acids from the C-terminus of SEQ ID NO:2. In yet another aspect, the variant further differs from SEQ ID NO:2 by a deletion of between about 28 and about 151 amino acids from the C-terminus of SEQ ID NO:2.

Another embodiment of the present invention relates to an isolated, recombinant human cystathionine β-synthase protein comprising no more than one or two amino acid residues at the N-terminus that is not a residue of the naturally occurring human cystathionine β-synthase amino acid sequence. The human cystathionine β-synthase protein can include an amino acid sequence selected from of: (a) positions 2-551 of SEQ ID NO:2; (b) an amino acid sequence that is at least about 70% identical to positions 2-551 of SEQ ID NO:2; or (c) an enzymatically active fragment of SEQ ID NO:2, wherein the fragment catalyzes the formation of cystathionine. In one aspect, the amino acid sequence further differs from positions 2-551 of SEQ ID NO:2 by at least one deletion or mutation of an amino acid residue of SEQ ID NO:2 selected from the group consisting of: Cys52 and His65 of SEQ ID NO:2, wherein the variant catalyzes the formation of cystathionine and has a reduced ability to bind heme. In another aspect, the enzymatically active fragment differs from positions 2-551 of SEQ ID NO:2 by a deletion of at least amino acid positions 2-39 of SEQ ID NO:2. In another aspect, the enzymatically active fragment differs from positions 2-551 of SEQ ID NO:2 by a deletion of at least amino acid positions 2-65 of SEQ ID NO:2. In yet another aspect, the enzymatically active fragment differs from positions 2-551 of SEQ ID NO:2 by a deletion of at least amino acid positions 2-70 or 2-71 of SEQ ID NO:2. In yet another aspect, the enzymatically active fragment differs from positions 2-551 of SEQ ID NO:2 by a deletion of at least amino acid positions 2-83 of SEQ ID NO:2. In another aspect, the enzymatically active fragment differs from positions 2-551 of SEQ ID NO:2 by a deletion of between about 1 and about 8 amino acids from the C-terminus of SEQ ID NO:2. In another aspect, the enzymatically active fragment differs from positions 2-551 of SEQ ID NO:2 by a deletion of between about 19 and about 169 amino acids from the C-terminus of SEQ ID NO:2. In yet another aspect, the enzymatically active fragment differs from positions 2-551 of SEQ ID NO:2 by a deletion of between about 28 and about 169 amino acids from the C-terminus of SEQ ID NO:2. In another aspect, the enzymatically active fragment differs from positions 2-551 of SEQ ID NO:2 by a deletion of between about 28 and about 151 amino acids from the C-terminus of SEQ ID NO:2.

In one embodiment of the invention, any of the above-described proteins and variants comprises no more than one or two amino acid residues at the N-terminus that is not a residue of the naturally occurring human cystathionine β-synthase amino acid sequence.

In one aspect, any of the above-described proteins and variants has specific activity that is at least about 0.5% of the specific activity of the wild-type human cystathionine β-synthase comprising SEQ ID NO:2. In another aspect, the protein or variant has specific activity that is at least about 1% of the specific activity of the wild-type human cystathionine β-synthase comprising SEQ ID NO:2. In another aspect, the protein or variant has specific activity that is at least about 10% of the specific activity of the wild-type human cystathionine β-synthase comprising SEQ ID NO:2. In yet another aspect, the protein or variant has specific activity that is at least about 20% of the specific activity of the wild-type human cystathionine β-synthase comprising SEQ ID NO:2.

Another embodiment of the present invention includes an isolated fusion protein comprising any of the above-described isolated human cystathionine β-synthase proteins or variants linked to a heterologous protein sequence.

Another embodiment of the present invention includes a composition comprising any of the above-identified isolated human cystathionine β-synthase proteins or variants.

Yet another embodiment of the present invention includes an isolated nucleic acid molecule comprising a nucleic acid sequence encoding any of the above-described human cystathionine β-synthase proteins or variants. Another aspect of the invention relates to a recombinant nucleic acid molecule comprising such a nucleic acid sequence, operatively linked to a expression control sequence. Another aspect of the invention relates to a recombinant host cell that is transfected with and expresses the recombinant nucleic acid molecule described above.

Another embodiment of the present invention relates to a method to treat homocystinuria, comprising administering to a patient any of the above-described human cystathionine β-synthase proteins or variants or a recombinant nucleic acid molecule encoding any of such proteins or variants.

Another embodiment of the invention relates to a method to produce a recombinant human cystathionine β-synthase. The method includes a first step of: (a) transfecting a recombinant host cell with a recombinant nucleic acid molecule comprising a first nucleic acid sequence encoding a human cystathionine β-synthase or homologue thereof having human cystathionine β-synthase biological activity, wherein the recombinant nucleic acid molecule comprises a recombinant expression vector operatively linked to the first nucleic acid sequence. The expression vector includes: (i) a second nucleic acid sequence encoding a fusion segment which is linked to the N-terminus of the first nucleic acid sequence by a linker region that will produce a human cystathionine β-synthase fusion protein comprising the fusion segment when the recombinant nucleic acid molecule is expressed; and (ii) a human rhinovirus 3C protease recognition sequence within the linker region. The 5' nucleotide of the nucleic acid sequence encoding the N-terminal amino acid residue of the human cystathionine β-synthase or homologue thereof is contiguous with the 3' nucleotide of the nucleic acid sequence encoding the two amino acid residues that occur immediately C-terminal to the human rhinovirus 3C protease recognition site, such that a human cystathionine β-synthase expressed by the recombinant nucleic acid molecule will contain at its N-terminus the two C-terminal amino acid residues of the human rhinovirus 3C protease recognition site. The method includes the additional steps of: (b) culturing the transfected host cell from (a) under conditions effective to produce the recombinant human cystathionine β-synthase fusion protein; (c) contacting the recombinant human cystathionine β-synthase fusion protein with a human rhinovirus 3C protease to cleave the fusion segment from the recombinant human cystathionine β-synthase; and (d) recovering the recombinant human cystathionine β-synthase as a substantially purified recombinant protein.

In one aspect of this method, the nucleic acid sequence encoding a human cystathionine β-synthase encodes a wild-type human cystathionine β-synthase comprising positions 3-551 of SEQ ID NO:2. In another aspect, the nucleic acid sequence encoding a human cystathionine β-synthase encodes a homologue of the wild type human cystathionine β-synthase that is at least about 70% identical to SEQ ID NO:2. In another aspect, the nucleic acid sequence encoding a human cystathionine β-synthase encodes a truncated isoform of the wild type human cystathionine β-synthase having enzymatic activity. In yet another aspect, the truncated isoform does not bind heme.

BRIEF DESCRIPTION OF THE DRAWINGS OF THE INVENTION

Figure 1:
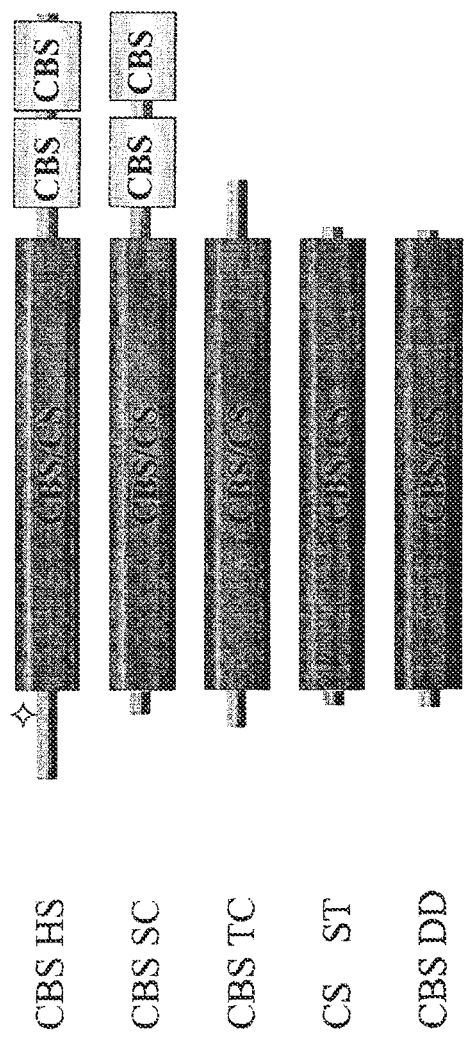
FIG. 1 is a schematic drawing showing a comparison of the domain organization of the CBS and CS enzymes from *Homo sapiens* and other organisms.

FIG. 5 is an alignment of human CBS (positions 1-123 and 363-551 of SEQ ID NO:2) with other related members of the P family of PLP-dependent enzymes, which illustrates amino acids that are conserved among the proteins (CBS_DM=positions 1-92 and 332-522 of SEQ ID NO:18; CBS_DD=positions 1-77 and 316-497 of SEQ ID NO:19; CBS_SC=positions 1-57 and 306-507 of SEQ ID NO:20; OASS_TA=positions 1-54 and 288-325 of SEQ ID NO:21; OASS_ST=positions 2-46 and 288-323 of SEQ ID NO:22).

DETAILED DESCRIPTION OF THE INVENTION

The present invention generally relates to human cystathionine β-synthase variants (e.g., homologues, fragments, mutants) and a method to produce recombinant human cystathionine β-synthase and variants thereof. More particularly, the present inventors have studied the role of both the N-terminal and C-terminal regions of human CBS by generating 11 sequential truncation mutants spanning residues 1-70 and 401-551 of SEQ ID NO:2 (see FIG. 2). All of these truncation mutants were expressed in *E. coli* and the effect of each deletion on activity, heme binding, response to AdoMet, oligomeric status and stability was determined. Characterization of these deletion mutants has shed new light upon the function and organization of the catalytic and regulatory regions of CBS, and has provided several new CBS variants with increased therapeutic value as compared to the wild-type enzyme.

Specifically, the human cystathionine β-synthase variants described herein are desirable for therapeutic applications (e.g., treatment of homocystinuria) because they have improved properties as compared to the wild-type protein. First, by way of example, enzymatically active variants of cystathionine β-synthase with reduced and preferably, eliminated, ability to bind heme are believed to be highly desirable for therapeutic applications because such proteins will not be able to release heme into the patient in vivo, thereby avoiding potentially toxic consequences that are possible when using the wild-type, heme-binding protein. Therefore, non-heme binding proteins are believed to be preferred for safe administration or expression of the protein in vivo. The present inventors have described herein variants of CBS, including CBS fusion proteins, that do not bind heme and which have enzymatic activity. In addition, truncated variants of the CBS protein are more manageable for in vitro production and in vivo administration or expression in vivo as transgenes. Moreover, many of the C-terminal deletion mutants described herein have improved specific activity as compared to the wild-type protein. However, even the CBS variants that have reduced activity, including severely reduced activity (e.g., the non-GST fusion Δ1-70 Δ401-551 CBS double deletion mutant), are believed to be highly useful for in vivo or ex vivo applications. Surprisingly, the present inventors have found that even very low CBS specific activity (e.g., less than 1%) is sufficient to produce a benefit via a useful increase in cystathionine and/or cysteine production. Therefore, CBS variant constructs having as little as 1% or less specific activity as compared to the wild-type CBS protein are useful in both in vitro and therapeutic applications of the invention. Moreover, the CBS variants of the present invention and nucleic acid molecules encoding the same are useful in vitro as enzymes for the production of cystathionine and, in conjunction with cystathionine γ-lyase, cysteine. Use of recombinant CBS and variants thereof to produce cystathionine in vitro replaces a cumbersome and lengthy organic chemistry synthesis. The enzymatically produced cystathionine will be all in one form rather than a mixture of stereoisomers produced chemically. CBS variants can also be used to remove or produce hydrogen sulfide. For example, removal of hydrogen sulfide is of concern in the production of beer.

In addition, the present inventors have discovered a method to express and purify recombinant human cystathionine β-synthase (CBS) and isoforms (variants) thereof which have only one or two additional amino acid residues at the N-terminus and which are believed to represent a highly desirable form of CBS for human therapeutic applications. As discussed above, the present inventors, without being bound by theory, believe that the addition of non-human, non-CBS amino acid residues at the N-terminus of the CBS protein as results from conventional recombinant production, alters the properties of the enzyme. In addition, human CBS is a desirable therapeutic reagent, but the presence of non-human, non-CBS residues at the N-terminus of the recombinant CBS protein may have serious consequences for therapeutic applications, since these residues may elicit the formation of antibodies against the recombinant protein in human patients. The present invention encompasses this novel method of expression for CBS, as well as the recombinantly expressed and purified forms of CBS produced thereby, which can be used in any of the in vivo or in vitro applications described above. For example, the CBS constructs described herein allow a) independent folding of the fusion partners with no impairment in the affinity chromatography; b) removal of the hinge region; and c) the resulting human wild-type protein differs from the one found in humans by the smallest amino acid, glycine, at the N-terminus. It is to be understood that this method of protein production is only one embodiment of the present invention which can be used to further enhance production of a CBS protein. The CBS variants disclosed herein can be produced by any suitable method, including any other conventional recombinant production method, and CBS proteins having in vivo and in vitro utility can be produced using any suitable method.

As discussed above, human CBS is a member of a large family of PLP-dependent enzymes that operate almost exclusively in the metabolism of amino acids. CBS belongs to the β family of PLP-dependent enzymes, members of which catalyze replacement and elimination reactions at Cβ. Human CBS displays significant levels of sequence and structural similarity with several other members of this family such as cysteine synthase (O-acetylserine sulfhydrylase, O-acetylserine (thiol)-lyase), serine/threonine deaminases, and the β subunit of tryptophan synthase (Meier et al., 2001, *Embo J.* 20(15), 3910-6). The present inventors have shown that the sequence and structural conservation between these enzymes is primarily confined to a region encompassed by residues 84-382 in human CBS (see FIG. 5). This region includes the PLP binding domain and is similar to, but more specifically defined than, the previously described, catalytically activated, protease resistant core of the enzyme spanning residues 40-413 of SEQ ID NO:2 (Kery et al., 1998, *Arch. Biochem. Biophys.* 355, 222-232).

The nucleic acid sequence encoding CBS and the amino acid sequence encoded thereby are available through GenBank Accession No. NM_000071, and these sequences are also disclosed in U.S. Pat. No. 5,523,225 to Kraus, which is incorporated herein by reference in its entirety. The coding sequence for CBS is represented herein as SEQ ID NO:1. SEQ ID NO:1 is a nucleic acid sequence encoding SEQ ID NO:2, which is the amino acid sequence for full-length human CBS, having 551 amino acid residues. The nucleic acid sequence of the genomic DNA encoding CBS is also publicly available through sequence databases.

Prior to the present invention, information regarding the functional domain organization of CBS has been derived from studies involving limited trypsinolysis (Kery et al., 1998, *Arch. Biochem. Biophys.* 355, 222-232) and the effects of various regulatory mutations (Shan et al., 2001, *Hum. Mol. Genet.* 10(6), 635-643; Janosik et al., 2001, *Acta Crystallogr. D Biol. Crystallogr.* 57(Pt 2), 289-291; Maclean et al., 2002, *Hum. Mutat.* 19(6), 641-55). The determination of the crystal structure of full-length CBS is problematic and complicated by the tendency of the protein to aggregate. In the absence of this information, the present inventors have used herein deletion studies to extend the knowledge of the functional domain organization of this protein.

Analysis of the various deletion mutants described herein, and particularly, the GST Δ1-70 Δ401-551 CBS double deletion mutant, has allowed the present inventors to further delineate the region of human CBS that is essential for catalysis. The fact that replacement of the N-terminal 70 residues with the unrelated GST fusion partner is sufficient and necessary for the formation of a significantly catalytically active form of this mutant indicates that the function of the N-terminal domain is primarily steric in nature. Similarly, the observation that this mutant protein remains stable and active after the subsequent removal of the GST fusion partner indicates that this region probably plays an essential role during the CBS folding pathway and/or assembly. The observed role of the GST fusion partner in stabilizing the double deletion mutant has important implications for studies designed to characterize the behavior of CBS mutants by heterologous expression in $E.$ $coli.$ A number of recent studies have investigated various CBS mutants solely as GST fusion proteins (Ojha et al., 2002, $Biochemistry$ 41(14), 4649-54; Kabil and Banerjee, 1999, $J.$ $Biol.$ $Chem.$ 274(44), 31256-60). The results presented herein indicate that this approach may generate artifactual results as the GST fusion partner is clearly capable of masking defects in CBS by assisting with folding and/or assembly and that its stabilizing effects can persist even after its removal from the assembled protein. Consequently, the behavior of the purified mutant protein may differ significantly from that observed in vivo.

The behavior of the $\Delta$1-39 mutant is also consistent with a role for the N-terminal domain in facilitating the correct folding of human CBS. This tetrameric mutant enzyme is induced ~4-fold by AdoMet but is intrinsically impaired in catalysis with only half the activity of wild type CBS. This impairment is unlikely to be due to a regulatory function as the scale of impairment is perfectly conserved in the AdoMet induced form of the protein. The deleterious effect of this deletion must be exerted during the folding and/or assembly of the protein as previous work in the present inventors' laboratory has shown that when these residues are removed from assembled full-length CBS by trypsin digestion, the resultant protein is not reduced in either catalytic activity or PLP binding (Kery et al., 1998, supra).

Prior to the present invention, the function of the evolutionarily non-conserved 70 N-terminal residues of mammalian CBS was unknown. The behavior of the $\Delta$1-70 N-terminal deletion mutant described herein offers insight into the function of this region and an explanation for its absence in CBS found in lower eukaryotes. The inventors show herein that when the $\Delta$1-70 $\Delta$401-551 deletion mutant is expressed as a GST fusion protein and the GST fusion partner is removed, the resultant protein has decreased affinity for PLP relative to that of the wild type. Previously, the inventors' laboratory has expressed CBS as a GST fusion protein lacking only the C-terminal domain and no such deficiency in PLP binding was observed (Janosik et al., 2001, $Acta$ $Crystallogr.$ $D$ $Biol.$ $Crystallogr.$ 57(Pt 2), 289-291), indicating that it is the lack of the 70 N-terminal residues that is responsible for the observed decrease in PLP binding. Yeast CBS lacks the N-terminal domain and also has a marked decrease in affinity for PLP relative to the human enzyme (Maclean et al., 2000, $J.$ $Inorg.$ $Biochem.$ 81(3), 161-71). This decreased affinity for PLP may reflect the fact that yeast are capable of endogenous de novo synthesis of pyridoxine (the metabolic precursor of PLP) while humans are dependent upon dietary sources. Without being bound by theory, the present inventors believe that it is conceivable that the N-terminal domain represents an evolutionary adaptation in mammals designed to augment retention of PLP by CBS.

The observation that the heme-free $\Delta$1-70 mutant is significantly impaired in catalysis (~20% of wild type) is consistent with a recent report on the activities of mutant forms of CBS that were severely depleted of heme by mutagenesis of either (but not both) of the heme binding residues Cys52 or His65 (Ojha et al., 2002, $Biochemistry$ 41(14), 4649-54). The function of the heme group was unknown at the time of the invention. An early hypothesis indicated that the heme group played a role in substrate activation by direct coordination of Hcy (Taoka et al., 1998, $J.$ $Biol.$ $Chem.$ 273, 25179-25184). However, discovery that the yeast enzyme does not require heme for catalysis (Maclean et al., 2000, $J.$ $Inorg.$ $Biochem.$ 81(3), 161-71; Jhee et al., 2000, $Biochemistry$ 39(34), 10548-56) and the subsequent observation that crystallized CBS is capable of catalysis after the displacement of the heme group by carbon monoxide (Bruno et al., 2001, $J.$ $Biol.$ $Chem.$ 276 (1), 16-19) all strongly indicated that the heme ligand is not directly involved in the condensation reaction catalyzed by CBS. The catalytic activity of the heme-free $\Delta$1-70 and $\Delta$1-70 $\Delta$401-551 deletion mutants also serve to disprove any direct catalytic role for heme indicating that the function of this ligand is likely to be regulatory and/or structural. Recent work from the present inventors' laboratory has indicated that deleterious oligomerization of mutant CBS molecules is associated with a concomitant loss of heme (Janosik et al., 2001, $Am.$ $J.$ $Hum.$ $Genet.$ 68(6), 1506-13). Data presented herein indicate that the heme-free deletion forms of CBS are also considerably less soluble than the wild type form and that the heme group has a significant influence upon the correct assembly of CBS.

The structural instability demonstrated by some of the partial C-terminal deletion mutants is consistent with the presence of a second CBS domain in the C-terminal regulatory region. The presence of this CBS2 domain was originally proposed on the basis of sequence similarity with the CBS domains present in the otherwise unrelated 1 MPDH enzyme (Shan et al., 2001, $Hum.$ $Mol.$ $Genet.$ 10(6), 635-643). The recent determination of the structure of the $S.$ $pyogenes$ IMPDH protein indicates that these two intrinsically hydrophobic domains are separate from the catalytic domain of the protein and are juxtaposed in order to minimize their hydrophobic interaction with the polar solvent (Zhang et al., 1999, $Biochemistry$ 38(15), 4691-700). The relative instability of the partial C-terminal deletion mutants compared to that of the larger deletion lacking both of the CBS domains, is consistent with a similar arrangement in CBS. In this scenario, removal of one of the CBS domains would induce destabilizing structural deformation of the protein as the remaining CBS domain seeks to minimize its interaction with the aqueous solvent while removal of both CBS domains would result in a stable active protein. The presence of dual CBS domains is evolutionarily conserved in the yeast CBS C-terminal region, which also appears to serve an autoinhibitory function albeit independent of AdoMet regulation (Jhee et al., 2000, $Biochemistry$ 39(34), 10548-56; Taoka and Banerjee, 2002, $J.$ $Biol.$ $Chem.$ 10, 10).

It has previously been reported that AdoMet is likely to bind CBS in a region localized between residues 421 and 469 in the previously defined CBS1 domain (Taoka et al., 1999, $Biochemistry$ 38(40), 13155-61). The rationale behind this assertion was that the D444N mutation contained within this region interfered with the CBS AdoMet response (Kluijtmans et al., 1996, $J.$ $Clin.$ $Invest.$ 98, 285-289). Subsequent work from the present inventors' laboratory has shown that mutations in this region can impair the CBS response to AdoMet without affecting the ability of the protein to bind AdoMet. Instead it was seen that CBS mutants containing these mutations, e.g. S466L, have already undergone the conformational change that is typically induced by AdoMet binding (Janosik et al., 2001, $Biochemistry$ 40(35), 10625-33). Additionally, point mutations in the second CBS2 domain located between residues 415 and 468 have been shown to impair AdoMet regulation although the effect of these mutations upon AdoMet binding was not investigated (Shan et al., 2001, *Hum. Mol. Genet.* 10(6), 635-643). The fact that deletion of 8 C-terminal residues can abolish the CBS response to AdoMet and constitutively activate the protein in a manner analogous to the previously described S466L mutation (Janosik et al., 2001, *Biochemistry* 40(35), 10625-33) indicates that the autoinhibitory function of the C-terminal region is not exclusively a function of the CBS domains. Without being bound by theory, it is possible that the deletion of these 8 terminal residues acts to interfere with the ability of CBS to bind AdoMet and it is possible that mutation of any or all of these residues will be capable of either disrupting the CBS AdoMet response or inducing constitutive activation.

The fold of the 1-413 truncated CBS enzyme belongs to the β-family of PLP enzymes (Alexander et al., 1994, *Eur. Biochem.* 219(3), 953-60). Another PLP containing enzyme, threonine deaminase (TD), shares the same fold of the catalytic domain and its domain organization seems to be analogous to CBS (Gallagher et al., 1998, *Structure* 6(4), 465-75). TD is also a homotetramer, with each subunit organized into an N-terminal catalytic domain (residues 1-320) and a C-terminal regulatory region (residues 321-514). The catalytic and regulatory domains are connected by a short "neck" that functions as a hinge, enabling the regulatory domain to rotate. It is possible that this arrangement allows the regulatory region to partially occlude the active site and thus modulate the catalytic efficiency of TD (Gallagher et al., 1998, *Structure* 6(4), 465-75). Superposition of both TD and CBS enzyme structures suggests that the regulatory domains of TD and CBS are located at similar positions. Clustal W alignment of the TD and CBS amino acid sequences reveals that the region in human CBS corresponding to the TD neck is represented by amino acids 383-394 of SEQ ID NO:2. These residues form an α-helix (helix 11) in CBS (Meier et al., 2001, *Embo J.* 20(15), 3910-6) that may also serve a hinge function during the AdoMet induced removal of the C-terminal domain from its zone of inhibition leading to greater active site accessibility.

Consideration of the oligomeric status of the various deletion mutants adds further evidence to the notion that the C-terminal domain is responsible for the assembly of CBS dimers into higher molecular weight oligomers. A recent report regarding CBS from *T. cruzi* found that this protein although clearly related to mammalian CBS, lacks the typical CBS C-terminal region and exists predominantly as a tetramer. As a result of these findings, these authors suggested that the C-terminal region of CBS is not exclusively responsible for the formation of tetramers (Nozaki et al., 2001, *J. Biol. Chem.* 276(9), 6516-23). However, the extensive deletion analysis presented in this paper indicates that the residues associated with tetramer formation reside exclusively in the C-terminal region and are located between residues 497 and 543 of SEQ ID NO:2. Consequently, the situation in *T. cruzi* is more likely to be an example of divergent evolution from a common ancestor. Site directed mutagenesis of specific residues and possibly internal deletions could enable characterization of which portions are specifically associated with the organization of CBS into higher molecular weight oligomers.

As used herein, reference to an isolated protein or polypeptide in the present invention, including an isolated cystathionine β-synthase protein (CBS protein), includes full-length proteins, fusion proteins, or any fragment or homologue (variant, mutant) of such a protein. Such a CBS protein can include, but is not limited to, purified CBS protein, recombinantly produced CBS protein, soluble CBS protein, insoluble CBS protein, and isolated CBS protein associated with other proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated CBS protein of the present invention is produced recombinantly. In addition, and by way of example, a "human CBS protein" refers to a CBS protein (generally including a homologue of a naturally occurring CBS protein) from a human (*Homo sapiens*) or to a CBS protein that has been otherwise produced from the knowledge of the structure (e.g., sequence) and perhaps the function of a naturally occurring CBS protein from *Homo sapiens*. In other words, a human CBS protein includes any CBS protein that has substantially similar structure and function of a naturally occurring CBS protein from *Homo sapiens* or that is a biologically active (i.e., has biological activity) homologue of a naturally occurring CBS protein from *Homo sapiens* as described in detail herein. As such, a human CBS protein can include purified, partially purified, recombinant, mutated/modified and synthetic proteins. According to the present invention, the terms "modification" and "mutation" can be used interchangeably, particularly with regard to the modifications/mutations to the amino acid sequence of CBS (or nucleic acid sequences) described herein. Similarly, the terms "homologue", "variant" and "mutant" can generally be used interchangeably herein, although those of skill in the art may prefer one term to another depending on the particular protein described.

As used herein, the term "homologue" (or variant or mutant) is used to refer to a protein or peptide which differs from a naturally occurring protein or peptide (i.e., the "prototype" or "wild-type" protein) by modifications to the naturally occurring protein or peptide, but which maintains the basic protein and side chain structure of the naturally occurring form. Such changes include, but are not limited to: changes in one, few, or even several amino acid side chains; changes in one, few or several amino acids, including deletions (e.g., a truncated version of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, changed, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in CBS homologues, as compared to the wild-type protein, either increase, decrease, otherwise change, or do not substantially change, the basic enzymatic activity of the CBS homologue as compared to the naturally occurring protein, cystathionine β-synthase. Some modifications in CBS homologues increase, decrease, otherwise change, or do not substantially change, other biological activities or properties of the CBS protein as compared to the naturally occurring protein (e.g., heme binding, response to AdoMet, oligomer formation, PLP binding). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased, increased, or different biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

According to the present invention, an isolated CBS protein, including a biologically active homologue or fragment thereof, has at least one characteristic of biological activity of activity a wild-type, or naturally occurring CBS protein (which can vary depending on the structure of the variant or homologue). The biological activity of CBS can include, but is not limited to, catalyzing the pyridoxal 5'-phosphate (PLP)-dependent condensation of serine and homocysteine to form cystathionine (i.e., the enzymatic activity or catalytic activity), binding of heme, PLP-binding, oligomer formation (e.g., dimerization or tetramerization), binding to AdoMet, and/or responsiveness to AdoMet. Methods of detecting and measuring CBS expression and biological activity include, but are not limited to, measurement of transcription of CBS, measurement of translation of CBS, measurement of binding or association of CBS with another protein (e.g., PLP, AdoMet), measurement of binding or association of CBS gene regulatory sequences to a protein or other nucleic acid, measurement of an increase or decrease in the catalytic (enzymatic) activity of CBS, measurement of heme binding by CBS, measurement of oligomer formation by CBS, and measurement of the response of CBS to binding by or association with another protein (e.g., CGL, cystathionine gamma lyase). Methods of measuring CBS catalytic activity, heme binding, PLP binding, AdoMet binding, AdoMet responsiveness, and oligomerization are known in the art and several of such methods are described in the Examples.

It is noted that an isolated CBS protein of the present invention (including homologues) is not required to have any of the above-identified CBS activities. A CBS protein can be a truncated, mutated or inactive protein, for example. Inactive CBS proteins are useful in some screening assays, for example (e.g., as a negative control), or for other purposes such as antibody production or, in the case of nucleotide sequences encoding inactive CBS proteins, as oligonucleotide probes or primers for the detection, amplification and/or isolation of CBS encoding nucleic acid sequences.

Methods to measure protein expression levels of CBS according to the invention include, but are not limited to: western blotting, immunocytochemistry, flow cytometry or other immunologic-based assays; assays based on a property of the protein including but not limited to, enzyme assays, ligand binding or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR).

Homologues of CBS can be products of protein or drug design or selection and can be produced using various methods known in the art. Such homologues can be referred to as mimetics. A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In one embodiment of the present invention, a CBS protein has an amino acid sequence that comprises, consists essentially of, or consists of, a truncated version of SEQ ID NO:2, including any of the truncated forms of SEQ ID NO:2 described herein. SEQ ID NO:2 represents a full-length human CBS protein of 551 amino acids (encoded by nucleic acid sequence SEQ ID NO:1. The present invention also includes other homologues of SEQ ID NO:2, including sequences having a given identity to SEQ ID NO:2 or a fragment thereof, and including homologues having no more than one or two non-CBS amino acid residues at the N-terminus. Preferably, the homologue has at least one CBS biological activity as described previously herein, and most preferably, has at least detectable CBS catalytic activity as described herein.

Preferred truncated forms of SEQ ID NO:2 according to the present invention include N-terminal deletion variants, C-terminal deletion variants, and variants having both N-terminal and C-terminal deletions. With regard to the N-terminal deletion variants, such variants include proteins that have an amino acid sequence that differs from SEQ ID NO:2 by at least one, and up to about 83 deleted amino acids from the N-terminal 83 amino acids of SEQ ID NO:2. Such variants can include any number of deletions from between position 1 and about 83 of SEQ ID NO:2, inclusive, in whole integers (e.g., a deletion of position 1, a deletion of positions 1-2, a deletion of positions 1-6, a deletion of positions 1-14, a deletion of positions 1-28, a deletion of positions 1-68, etc., and any number in between, up to a deletion of all of positions 1-83). Preferred deletion variants include, but are not limited to, variants having a deletion of amino acid positions (relative to SEQ ID NO:2) of about position 1, from about 1-39, about 1-52, about 1-65, about 1-69, about 1-70, or about 1-83. Such variants would have a starting amino acid position, relative to SEQ ID NO:2, of about 2, 40, 53, 66, 70, 71, or 84, respectively. Any other starting position between 2 and 84 is also specifically encompassed by the invention, without the need to explicitly name each and every amino acid position between 2 and 84. Any of the N-terminal deletion mutants described herein can comprise the remainder of the full-length CBS sequence (e.g., all the way to positions 551 of SEQ ID NO:2), or they can include any of the C-terminal truncations as described herein, or other internal modifications (mutations) as compared to the wild-type CBS sequence as described herein. Preferably, these CBS variants of the invention catalyze the formation of cystathionine and may have one, more or all of the other biological activities of a wild-type CBS protein.

In a preferred embodiment, a CBS variant of the invention has one or more mutations or deletions that result in decreased heme binding by the variant and preferably, in substantially no heme binding by the variant. In one aspect of the invention, a non-heme binding CBS protein is produced by deletion of from between about 65 and about 83 of the N-terminal amino acids of SEQ ID NO:2, including any number of N-terminal amino acids in whole integers between about 65 amino acids (i.e., about positions 1-65 of SEQ ID NO:2) and about 83 (i.e., about positions 1-83 of SEQ ID NO:2). Therefore, such a truncated variant (deletion mutant) of SEQ ID NO:2 would have a starting, or first, amino acid position, relative to SEQ ID NO:2, of one of positions from about 66 through about position 84, where the largest possible deletion would result in a protein that had a first amino acid at about position 84 of SEQ ID NO:2. Preferred variants include CBS deletion mutants having a deletion of amino acid positions (relative to SEQ ID NO:2) from about positions 1-65, about 1-69, about 1-70, or about 1-83. Such variants would have a starting amino acid position, relative to SEQ ID NO:2, of about 66, 70, 71, or 84, respectively. Any other starting position between 66 and 84 is also specifically encompassed by the invention, without the need to explicitly name each and every amino acid position between 66 and 84. Preferably, these CBS variants of the invention catalyze the formation of cystathionine and do not bind heme.

In one aspect of the invention related to N-terminal deletions that produce non-heme binding CBS variants, the protein differs from SEQ ID NO:2 by at least a deletion or mutation of Cys52 and His65 of SEQ ID NO:2. As discussed previously herein, Cys52 and His65 are the thiolate and histidine ligands to heme. Prior to the present invention, variants in which both of these residues are mutated to significantly reduce and preferably abolish heme binding have not been described. A CBS variant with a mutation or deletion of these two residues can have any other additional modifications to the N- or C-terminus of the protein as described herein, and/or can be homologues related to the wild-type CBS protein of SEQ ID NO:2 by a given percent identity, also as described elsewhere herein. Preferably, these CBS variants of the invention catalyze the formation of cystathionine and do not bind heme.

With regard to the C-terminus of the CBS variants of the invention, such variants include proteins that have an amino acid sequence that differs from SEQ ID NO:2 by at least one, and up to about 169, deleted amino acids from the C-terminal 169 amino acids of SEQ ID NO:2 (the C-terminal 169 amino acids of SEQ ID NO:2 are positions 383-551 of SEQ ID NO:2). Such variants can include any number of deletions from between position 551 and about 383 of SEQ ID NO:2, inclusive, in whole integers (e.g., a deletion of position 551, a deletion of positions 550-551, a deletion of positions 544-551, a deletion of positions 482-551, a deletion of positions 437-551, a deletion of positions 391-551, etc., and any number in between, up to a deletion of all of positions 383-551). Preferred deletion variants include, but are not limited to, variants having a deletion of amino acid positions (relative to SEQ ID NO:2) of from about 544-551, about 524-551, about 497-551, about 489-551, about 442-551, about 414-551, about 401-551, or 383-551. Such variants would have an ending amino acid position, relative to SEQ ID NO:2, of about 543, 523, 496, 488, 441, 413, 400 or 382, respectively. Any other ending position between 550 and 382 is also specifically encompassed by the invention, without the need to explicitly name each and every amino acid position between 550 and 382 of SEQ ID NO:2. However, in a preferred embodiment, a CBS variant of the invention preferably does not include a C-terminal deletion of between 534-551 (end of protein is position 533). In another preferred embodiment, the CBS variant of the invention preferably does not include a C-terminal deletion of any of the possible combinations between 534-551 (end is 533) and 543-551 (end of protein is 542)—in other words, the truncated CBS variant should be either longer than a 543-551 deletion mutant or is shorter than a 534-551 deletion mutant. In another preferred embodiment, the CBS variant of the invention preferably does not include a C-terminal deletion of between 525-551 (end of protein is 524) and 543-551 (end of protein is 542)—in other words the truncated CBS variant should be either longer than a 543-551 deletion mutant or shorter than a 525-551 deletion mutant. These last two exclusions are based on data generated by the inventors that at least a mutant having a deletion of 534-551 (end of protein is 533) was not stable enough for production under the conditions tested. However, the use of other production methods, including stabilization via linkage to a fusion protein, may allow production of this variant, and so it is not excluded from the invention. Further, the addition or deletion of even one more amino acid to this variant may result in sufficient stability and activity to produce the protein by the exemplified method, as longer and shorter variants were produced by the present inventors (see Examples). Any of the C-terminal deletion mutants described herein can comprise the remainder of the full-length CBS sequence (e.g., all the way to position 1 of SEQ ID NO:2), or they can include any of the N-terminal truncations as described herein, or other internal modifications (mutations) as compared to the wild-type CBS sequence as described herein. Preferably, any of the above-described CBS variants of the invention catalyze the formation of cystathionine and may have one, more or all of the other biological activities of a wild-type CBS protein.

In one embodiment of the invention, a CBS variant can include any combination of the N-terminal deletions or modifications and the C-terminal deletions described herein. In another embodiment additional modifications can be achieved by modification of other amino acid residues to provide a given percent identity to the wild-type CBS sequence.

In one embodiment, any of the CBS variants described herein has no more than one or two non-CBS amino acid residues at the N-terminus (i.e., the variant comprises no more than one or two amino acid residues at the N-terminus that is/are not a residue of the naturally occurring human cystathionine β-synthase amino acid sequence at that position). Such a variant can be produced, for example, using the novel method of recombinant CBS production described below. Such variants can also include a full length CBS protein comprising SEQ ID NO:2 or a homologue of SEQ ID NO:2 as described herein, wherein the protein has no more than one or two non-CBS amino acid residues at the N-terminus.

In one embodiment, any of the above-described CBS variants of the present invention, including any truncated CBS protein, comprises, consists essentially of, or consists of, an amino acid sequence that is at least about 60% identical, or at least about 65% identical, or at least about 70% identical, or at least about 75% identical, or at least about 80% identical, or at least about 85% identical, or at least about 90% identical, or at least about 95% identical, or at least about 96% identical, or at least about 97% identical, or at least about 98% identical, or at least about 99% identical, to the wild-type amino acid sequence represented by SEQ ID NO:2, or to a biologically active truncation thereof (including non-heme-binding, but catalytically active variants).

A CBS protein of the present invention comprises an amino acid sequence that is less than 100% identical to SEQ ID NO:2, and in another embodiment, is less than about 99% identical to SEQ ID NO:2, and in another embodiment, is less than 98% identical to SEQ ID NO:2, and in another embodiment, is less than 97% identical to SEQ ID NO:2, and in another embodiment, is less than 96% identical to SEQ ID NO:2, and in another embodiment, is less than 95% identical to SEQ ID NO:2, and in another embodiment, is less than 94% identical to SEQ ID NO:2, and in another embodiment, is less than 93% identical to SEQ ID NO:2, and in another embodiment, is less than 92% identical to SEQ ID NO:2, and in another embodiment, is less than 91% identical to SEQ ID NO:2, and in another embodiment, is less than 90% identical to SEQ ID NO:2, and so on, in increments of whole integers.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=−2
  Open gap (5) and extension gap (2) penalties
  gap x_dropoff (50) expect (10) word size (11) filter (on)
For blastp, using 0 BLOSUM62 matrix:
  Open gap (11) and extension gap (1) penalties
  gap x_dropoff (50) expect (10) word size (3) filter (on).

A CBS protein can also include proteins having an amino acid sequence comprising at least 10 contiguous amino acid residues of SEQ ID NO:2 (i.e., 10 contiguous amino acid residues having 100% identity with 10 contiguous amino acids of SEQ ID NO:2). In other embodiments, a homologue of a CBS amino acid sequence includes amino acid sequences comprising at least 20, or at least 30, or at least 40, or at least 50, or at least 75, or at least 100, or at least 125, or at least 150, or at least 175, or at least 150, or at least 200, or at least 250, or at least 300, or at least 350, or at least 400, or at least 450, or at least 500, or at least 550, contiguous amino acid residues of the amino acid sequence represented by SEQ ID NO:2, and any whole integer in between 10 and 550 contiguous amino acid residues. In a preferred embodiment, a CBS homologue has measurable or detectable CBS biological activity.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

One of skill in the art will be able to readily produce and identify CBS homologues according to the invention, and particularly, CBS homologues having CBS biological activity, and CBS homologues have catalytic activity but not heme-binding activity, as described herein. The present inventors have provided an alignment of CBS and other related members of the β family of PLP-dependent enzymes in FIG. 5, which illustrates amino acids that are conserved among the proteins. In particular, the most conserved region of amino acids spans positions 84-382 of SEQ ID NO:2. Referring to FIG. 5, this figure shows a comparison of CBS and CS amino acid sequences from *Homo sapiens* and other organisms (HS, *Homo sapiens* (Swiss-Prot Accession No. P35520); DM, *Drosophila Melanogaster* (Entrez Accession No. AAF50863.1, gene product CG 1753); DD, *Dictyostelium discoideum* (Swiss-Prot Accession No. P46794); SC, *Saccharomyces cerevisiae* (Swiss-Prot Accession No. P32582); TA, *Triticum aestivum* (Swiss-Prot Accession No. P38076); ST, *Salmonella typhimurium* (Swiss-Prot Accession No. P12674). The sequences were aligned using the CLUSTAL W (1.81) multiple sequence alignment software using clustalw_mp CPU mode, while other settings were default. Asterisks indicate identical amino acids, dots indicate semiconservative replacement. The shaded residues represent a CBS domain that is present in two copies in yeast CBS. Human CBS contains one well-conserved copy of this motif (CBS1); the second CBS domain (CBS2) has been predicted based on sequence similarity with other CBS domain containing protein, IMPDH from *S. pyogenes*. The PLP binding lysine residue is marked with triangle. Residues responsible for heme binding in human CBS (Cys52 and His65) are marked with a square. Dotted lines indicate a break in the sequence.

The effects of the presence or absence of various portions of the N- or C-terminal portion of human CBS are described by a detailed analysis for the first time herein. The alignment in FIG. 5 provides one of skill in the art with guidance as to which amino acids will be most likely to tolerate change in the production of CBS homologues of the invention. The present inventors have also demonstrated through the production of CBS deletion mutants, that as much as 40% of the wild-type CBS protein may be deleted and still result in a CBS homologue that has catalytic activity.

In another embodiment, a CBS variant, including any of the CBS variants (homologues) described herein, includes a protein having an amino acid sequence that is sufficiently similar to a natural CBS amino acid sequence that a nucleic acid sequence encoding the homologue is capable of hybridizing under moderate, high or very high stringency conditions (described below) to (i.e., with) a nucleic acid molecule encoding the natural CBS protein (i.e., to the complement of the nucleic acid strand encoding the natural CBS amino acid sequence). Preferably, a homologue of a CBS protein is encoded by a nucleic acid molecule comprising a nucleic acid sequence that hybridizes under low, moderate, or high stringency conditions to the complement of a nucleic acid sequence that encodes a protein comprising an amino acid sequence represented by SEQ ID NO:2 or any of the truncated forms thereof described herein. Such hybridization conditions are described in detail below.

A nucleic acid sequence complement of nucleic acid sequence encoding a CBS protein of the present invention refers to the nucleic acid sequence of the nucleic acid strand that is complementary to the strand which encodes CBS. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence such as SEQ ID NO:2, and/or with the complement of the nucleic acid sequence that encodes an amino acid sequence such as SEQ ID NO:2. Methods to deduce a complementary sequence are known to those skilled in the art. It should be noted that since nucleic acid sequencing technologies are not entirely error-free, the sequences presented herein, at best, represent apparent sequences of a CBS protein of the present invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Nat) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M NaI at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

The minimum size of a protein and/or homologue of the present invention is a size sufficient to have at least one CBS biological activity or, when the protein is not required to have such activity, sufficient to be useful for another purpose associated with a CBS protein of the present invention. In one embodiment, the CBS variant protein of the present invention is at least 250 amino acids in length, or at least about 275 amino acids in length, or at least about 300 amino acids in length, or at least about 325 amino acids in length, or at least about 350 amino acids in length, or at least about 375 amino acids in length, or at least about 400 amino acids in length, or at least about 425 amino acids in length, or at least about 450 amino acids in length, or at least about 500 amino acids in length, or at least about 525 amino acids in length, or at least about 550 amino acids in length, up to a full length CBS protein, and including any size in between 250 and 551 amino acids in increments of one whole integer (one amino acid). There is no limit, other than a practical limit, on the maximum size of such a protein in that the protein can include a portion of a CBS protein or a full-length CBS protein, plus additional sequence (e.g., a fusion protein sequence), if desired.

Similarly, the minimum size of a nucleic acid molecule of the present invention is a size sufficient to encode a protein having the desired CBS activity, sufficient to encode a protein comprising at least one epitope which binds to an antibody, or sufficient to form a probe or oligonucleotide primer that is capable of forming a stable hybrid with the complementary sequence of a nucleic acid molecule encoding a natural CBS protein (e.g., under moderate, high, or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include any portion of a CBS protein encoding sequence.

The present invention also includes a fusion protein that includes a CBS variant-containing domain (including any of the CBS variants described herein) attached to one or more fusion segments, which are typically heterologous in sequence to the CBS sequence (i.e., different than CBS sequence). Suitable fusion segments for use with the present invention include, but are not limited to, segments that can: enhance a protein's stability; provide other desirable biological activity; and/or assist with the purification of CBS (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the CBS variant-containing domain of the protein and can be susceptible to cleavage in order to enable straight-forward recovery of the protein. Fusion proteins are preferably produced by culturing a recombinant cell transfected with a fusion nucleic acid molecule that encodes a protein including the fusion segment attached to either the carboxyl and/or amino terminal end of a CBS variant-containing domain. For example, some preferred fusion segments for use in a CBS variant fusion protein include, but are not limited to, glutathione S-transferase (GST), His tag, and Strep tag.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

Further embodiments of the present invention include nucleic acid molecules that encode a CBS protein. A nucleic acid molecule of the present invention includes a nucleic acid molecule comprising, consisting essentially of, or consisting of, a nucleic acid sequence encoding any of the isolated CBS variants described herein. In a preferred embodiment a nucleic molecule of the present invention includes a nucleic acid molecule comprising, consisting essentially of, or consisting of, a nucleic acid sequence represented by a homologue of SEQ ID NO:1 which differs from SEQ ID NO:1 in that it encodes a specified CBS variant of SEQ ID NO:2 as described herein. A nucleic acid molecule of the present invention can include the complementary sequence or an oligonucleotide of any of the nucleic acid sequences described herein.

In one embodiment, such nucleic acid molecules include isolated nucleic acid molecules that hybridize under moderate stringency conditions, and more preferably under high stringency conditions, and even more preferably under very high stringency conditions, as described above, with the complement of a nucleic acid sequence encoding a naturally occurring CBS protein (i.e., including naturally occurring allelic variants encoding a CBS protein). Preferably, an isolated nucleic acid molecule encoding a CBS variant of the present invention comprises a nucleic acid sequence that hybridizes under moderate, high, or very high stringency conditions to the complement of a nucleic acid sequence that encodes a protein comprising a CBS amino acid sequence that is one of the variants of SEQ ID NO:2 described herein.

In accordance with the present invention, an isolated nucleic acid molecule is a nucleic acid molecule (polynucleotide) that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. An isolated CBS-encoding nucleic acid molecule of the present invention (i.e., a nucleic acid molecule encoding a CBS variant as described herein) can be isolated from its natural source or produced using recombinant DNA technology (e.g., polymerase chain reaction (PCR) amplification, cloning) or chemical synthesis. Isolated CBS nucleic acid molecules can include or be derived from, for example, CBS genes, natural allelic variants of CBS genes, CBS coding regions or portions thereof, and CBS coding and/or regulatory regions modified by nucleotide insertions, deletions, substitutions, and/or inversions in a manner such that the modifications do not substantially interfere with the nucleic acid molecule's ability to encode a CBS variant of the present invention or to form stable hybrids under stringent conditions with natural gene isolates. An isolated CBS variant-encoding nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a CBS variant protein of the present invention can vary due to degeneracies. It is noted that a nucleic acid molecule of the present invention is not required to encode a protein having CBS protein activity, or all CBS protein activities. A nucleic acid molecule can encode a truncated, mutated or inactive protein, for example. Such nucleic acid molecules and the proteins encoded by such nucleic acid molecules are useful in as probes and primers for the identification of other CBS proteins. If the nucleic acid molecule is an oligonucleotide, such as a probe or primer, the oligonucleotide preferably ranges from about 5 to about 50 or about 500 nucleotides, more preferably from about 10 to about 40 nucleotides, and most preferably from about 15 to about 40 nucleotides in length.

According to the present invention, reference to a CBS gene includes all nucleic acid sequences related to a natural (i.e. wild-type) CBS gene, such as regulatory regions that control production of the CBS protein encoded by that gene (such as, but not limited to, transcription, translation or post-translation control regions) as well as the coding region itself. In another embodiment, a CBS gene can be a naturally occurring allelic variant that includes a similar but not identical sequence to the nucleic acid sequence encoding a given CBS protein. Allelic variants have been previously described above. The phrases "nucleic acid molecule" and "gene" can be used interchangeably when the nucleic acid molecule comprises a gene as described above.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on protein biological activity. Allelic variants and protein homologues (e.g., proteins encoded by nucleic acid homologues) have been discussed in detail above.

A CBS nucleic acid molecule homologue (i.e., encoding a CBS variant as described herein can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a CBS variant is gene shuffling (i.e., molecular breeding) (See, for example, U.S. Pat. No. 5,605,793 to Stemmer; Minshull and Stemmer; 1999, *Curr. Opin. Chem. Biol.* 3:284-290; Stemmer, 1994, *P.N.A.S. USA* 91:10747-10751, all of which are incorporated herein by reference in their entirety). This technique can be used to efficiently introduce multiple simultaneous changes in the CBS protein. Nucleic acid molecule homologues can be selected by hybridization with a CBS gene or by screening the function of a protein encoded by a nucleic acid molecule (i.e., biological activity).

One embodiment of the present invention relates to a recombinant nucleic acid molecule which comprises any of the isolated nucleic acid molecules described above which are operatively linked to at least one expression control sequence. More particularly, according to the present invention, a recombinant nucleic acid molecule typically comprises a recombinant vector and the isolated nucleic acid molecule as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically a contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell, although it is preferred if the vector remain separate from the genome for most applications of the invention. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., the CBS variant) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

In another embodiment of the invention, the recombinant nucleic acid molecule comprises a viral vector. A viral vector includes an isolated nucleic acid molecule of the present invention integrated into a viral genome or portion thereof, in which the nucleic acid molecule is packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

Typically, a recombinant nucleic acid molecule includes at least one nucleic acid molecule of the present invention operatively linked to one or more expression control sequences. As used herein, the phrase "recombinant molecule" or "recombinant nucleic acid molecule" primarily refers to a nucleic acid molecule or nucleic acid sequence operatively linked to an expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence in a manner such that the molecule is able to be expressed when transfected (i.e., transformed, transduced, transfected, conjugated or conduced) into a host cell. Expression control sequences are sequences which control the initiation, elongation, or termination of transcription and/or translation. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced. Expression control sequence can also include additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture (described above) after they become cancerous, for example. Therefore, to avoid confusion, the term "transfection" is preferably used with regard to the introduction of exogenous nucleic acids into animal cells or insect cells, and is used herein to generally encompass transfection of animal cells and insect cells and transformation of plant cells and microbial cells, to the extent that the terms pertain to the introduction of exogenous nucleic acids into a cell. Therefore, transfection techniques include, but are not limited to, transformation, particle bombardment, electroporation, microinjection, lipofection, adsorption, infection and protoplast fusion.

One or more recombinant molecules of the present invention can be used to produce an encoded product (e.g., a CBS variant) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, or animal cell that can be transfected. Host cells can be either untransfected cells or cells that are already transfected with at least one other recombinant nucleic acid molecule.

In one embodiment, one or more protein(s) expressed by an isolated nucleic acid molecule of the present invention are produced by culturing a cell that expresses the protein (i.e., a recombinant cell or recombinant host cell) under conditions effective to produce the protein. In some instances, the protein may be recovered, and in others, the cell may be harvested in whole (e.g., for ex vivo administration), either of which can be used in a composition. A preferred cell to culture is any suitable host cell as described above. Effective culture conditions include, but are not limited to, effective media, bioreactor, temperature, pH and oxygen conditions that permit protein production and/or recombination. An effective medium refers to any medium in which a given host cell is typically cultured. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the culture medium; be secreted into a space between two cellular membranes; or be retained on the outer surface of a cell membrane. The phrase "recovering the protein" refers to collecting the whole culture medium containing the protein and need not imply additional steps of separation or purification. Proteins produced according to the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Methods for producing and recovering CBS proteins according to the present invention are described in detail in the Examples section.

Proteins of the present invention are preferably retrieved, obtained, and/or used in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is substantially free of contaminants, other proteins and/or chemicals that might interfere or that would interfere with its use in a method disclosed by the present invention, or that at least would be undesirable for inclusion with an CBS protein (including homologues) when it is used in a method disclosed by the present invention. Such methods include enzymatic reactions (e.g., production of cystathionine), preparation of therapeutic compositions, administration in a therapeutic composition, and all other methods disclosed herein. Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the CBS protein is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

One embodiment of the present invention relates to a method to recombinantly produce and purify a human cystathionine β-synthase. The method includes the step of cloning a nucleic acid sequence encoding a human CBS enzyme or an isoform thereof into a an expression vector that includes: (a) a cloning site that will link a fusion partner (e.g., glutathione S-transferase, or GST) to the nucleic acid sequence to be expressed, and (b) a protease cleavage recognition site for the human rhinovirus 3C protease (e.g., available from Pharmacia as a fusion protein called PreScission™) or for a protease using a similar cleavage site, for cleaving the fusion partner from the CBS protein after expression of the recombinant fusion protein. As part of the invention, the expression vector is first genetically modified for the specific introduction of a CBS-encoding nucleic acid sequence which will result in expression of a CBS-fusion protein that can be cleaved by the human rhinovirus 3C protease such that a CBS protein having only one additional non-CBS, N-terminal amino acid residue is produced. This result is not possible using the unmodified multiple cloning site in the commercially available vector. The CBS-encoding nucleic acid sequence is introduced into the genetically modified vector, the recombinant fusion protein is expressed and purified using conventional methods or those suitable for CBS production (e.g., see U.S. Pat. No. 5,635,375, supra), and finally, the fusion partner and all but one of the non-CBS amino acid residues is cleaved from the CBS protein, leaving a highly purified, nearly completely human recombinant CBS protein which is ideal for use in human therapeutic applications.

One embodiment of the present invention makes use of the discovery by the present inventors that an expression vector which includes a cleavage site for the human rhinovirus 3C protease can be manipulated so that the last two amino acid residues of the protease cleavage recognition sequence can be used to form the first two amino acid residues of the expressed human CBS protein. The last amino acid residue of the 8-amino acid protease cleavage recognition sequence (represented herein by SEQ ID NO:17) is the same as the second amino acid residue in the wild-type CBS protein. The human rhinovirus 3C protease cleaves the recognition sequence just prior to the last two amino acid residues (i.e., positions 7 and 8 of SEQ ID NO:17), thereby allowing the cleavage of a CBS protein having one or two non-CBS amino acid at the N-terminus. Although many constructs will have two non-CBS amino acids at the N-terminus (i.e., the last two amino acids from the rhinovirus protease recognition site, or positions 7-8 of SEQ ID NO:2), some CBS variants will have only one non-CBS residue at the N-terminus. For example, in the case of the wild-type protein, the way the construct is formed, positions 7-8 of SEQ ID NO:17 are linked directly to positions 3-551 of the CBS protein (SEQ ID NO:2). The second of the two residues encoded by the protease recognition sequence (i.e., Pro8 of SEQ ID NO:17) is the same as the second residue of the natural CBS sequence (i.e., Pro2 of SEQ ID NO:2). Therefore, the Pro inserted prior to position 3 of the natural CBS sequence is the same as the natural CBS residue at that position and therefore is not technically a non-CBS residue. This leaves only a glycine substitution (i.e., the Gly7 of SEQ ID NO:17) for the natural Met at position 1 of the CBS protein. In the case of at least the 1-70 N-terminal deletion mutant, the second of the two protease recognition sequence amino acid residues (Pro 8 of SEQ ID NO:17) is the same as the natural CBS residue at position 70 (Pro70 of SEQ ID NO:2), effectively producing a truncated protein with only one non-CBS residue (effectively a 1-69 deletion mutant with one additional heterologous residue, Gly, at the N-terminus).

The present inventors also realized that the long cleavage recognition sequence of the human rhinovirus 3C protease could serve as a hinge region between the two fusion partners allowing them to fold independently and allow for interaction of the GSH protein with the affinity resin. Because the actual cleavage of the 8 amino acid long protein recognition sequence occurs near the C-terminus of this region, most of the hinge can be removed from the N-terminus of CBS by the protease. Similar manipulations for expression of isoforms (homologues) of the CBS enzyme will be apparent after reading this description and the Examples. In the unmodified expression vector, the protease cleavage site is upstream of the poly linker and the multiple cloning site, which would produce a recombinant protein having several additional N-terminal, non-CBS residues, similar to that produced with other conventional expression vectors. This method of the invention is described in detail in the Examples section.

Some embodiments of the present invention include a composition comprising any of the CBS variants described herein for in vitro cystathionine or cysteine production, to remove or produce hydrogen sulfide in vitro, or for therapeutic uses in vivo (e.g., to treat or prevent homocystinuria and conditions related thereto). Therefore, another embodiment of the invention relates to a composition comprising an isolated CBS variant or a nucleic acid is molecule (including recombinant nucleic acid molecules) encoding such a variant. The composition typically also includes a pharmaceutically acceptable carrier. In this aspect of the present invention, an isolated CBS variant can be any of the CBS variants previously described herein. The compositions and their components can be used in any of the in vitro or therapeutic embodiments of the invention described herein.

Compositions of the present invention are useful for regulating biological processes and particularly, processes associated with the catalysis of the pyridoxal 5'-phosphate (PLP)-dependent condensation of serine and homocysteine to form cystathionine. In particular, compositions of the present invention are useful for producing cystathionine and cysteine in vitro or for treating a patient that will benefit from increased CBS activity (e.g., a patient with homocystinuria).

According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where it is desirable to regulate CBS activity. Preferred pharmaceutically acceptable carriers are capable of maintaining a protein or recombinant nucleic acid molecule of the present invention in a form that, upon arrival of the protein or recombinant nucleic acid molecule at the target cell or tissue in a culture or in patient, the protein or recombinant nucleic acid molecule is capable of interacting with its target (e.g., a substrate for CBS).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposomes, and transdermal delivery systems. Other carriers of the present invention include liquids that, upon administration to a patient, form a solid or a gel in situ. Preferred carriers are also biodegradable (i.e., bioerodible). When the compound is a recombinant nucleic acid molecule, suitable carriers include, but are not limited to liposomes, viral vectors or other carriers, including ribozymes, gold particles, poly-L-lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a patient, thereby targeting and making use of a protein or nucleic acid of the present invention at that site. A pharmaceutically acceptable carrier which is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One delivery vehicle that could be used in the present invention is a liposome. A liposome is capable of remaining stable in an animal for a sufficient amount of time to deliver a nucleic acid molecule described in the present invention to a preferred site in the animal. A liposome, according to the present invention, comprises a lipid composition that is capable of delivering a nucleic acid molecule or protein described in the present invention to a particular, or selected, site in a patient. A liposome according to the present invention comprises a lipid composition that is capable of fusing with the plasma membrane of the targeted cell to deliver a nucleic acid molecule or protein into a cell. Suitable liposomes for use with the present invention include any liposome. Preferred liposomes of the present invention include those liposomes commonly used in, for example, gene delivery or protein delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or protein of the present invention can be achieved using methods standard in the art.

Another preferred delivery vehicle comprises a viral vector. A viral vector includes an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

Another embodiment of the present invention relates to a method to regulate biological processes, including cystathionine production, by regulating the expression and/or activity of CBS. This embodiment can generally include the use (e.g., administration) of therapeutic compositions comprising one or more of the CBS variants or nucleic acid molecules encoding such variants, that are useful in a method of regulating the production of cystathionine that are mediated by or associated with the expression and biological activity of CBS.

Accordingly, in one embodiment, the method of the present invention preferably regulates cystathionine production in a culture or in a patient. In the case of the patient, the patient is preferably protected from or treated for a disease that is amenable to regulation of cystathionine production, such as homocystinuria and conditions/symptoms related thereto (e.g., dislocated optic lenses, skeletal disorders, mental retardation and premature arteriosclerosis and thrombosis). As used herein, the phrase "protected from a disease" refers to reducing the symptoms of the disease; reducing the occurrence of the disease, and/or reducing the severity of the disease. Protecting a patient can refer to the ability of a therapeutic composition of the present invention, when administered to a patient, to prevent to a disease from occurring and/or to cure or to treat the disease by alleviating disease symptoms, signs or causes. As such, to protect a patient from a disease includes both preventing disease occurrence (prophylactic treatment) and treating a patient that has a disease or that is experiencing initial symptoms or later stage symptoms of a disease (therapeutic treatment). The term, "disease" refers to any deviation from the normal health of a patient and includes a state when disease symptoms are present, as well as conditions in which a deviation (e.g., infection, gene mutation, genetic defect, etc.) has occurred, but symptoms are not yet manifested (e.g., a predisease condition).

More specifically, a therapeutic composition as described herein, when administered to a patient by the method of the present invention, preferably produces a result which can include alleviation of the disease (e.g., reduction of at least one symptom or clinical manifestation of the disease), elimination of the disease, alleviation of a secondary disease resulting from the occurrence of a primary disease, or prevention of the disease.

According to the present invention, an effective administration protocol (i.e., administering a therapeutic composition in an effective manner) comprises suitable dose parameters and modes of administration that result in the desired effect in the patient (e.g., an increase in the activity of cystathionine β-synthase in the patient or an increase in the condensation of serine and homocysteine to form cystathionine, preferably so that the patient is protected from the disease (e.g., by disease prevention or by alleviating one or more symptoms of ongoing disease). Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that results in regulation of CBS activity or formation of cystathionine or cysteine in a patient, or in the amelioration of at least one symptom of a condition in the patient, when administered one or more times over a suitable time period. Doses can vary depending upon the disease being treated. One of skill in the art can readily determine appropriate single dose sizes for a given patient based on the size of a patient and the route of administration.

In one aspect of the invention, a suitable single dose of a therapeutic composition of the present invention is an amount that, when administered by any route of administration, regulates at least one parameter of CBS expression or biological activity in the cells of the patient as described above, as compared to a patient which has not been administered with the therapeutic composition of the present invention (i.e., a pre-determine control patient or to measurement), as compared to the patient prior to administration of the composition, or as compared to a standard established for the particular disease, patient type and composition.

As discussed above, a therapeutic composition of the present invention is administered to a patient in a manner effective to deliver the composition to a cell, a tissue, and/or systemically to the patient, whereby the desired result is achieved as a result of the is administration of the composition. Suitable administration protocols include any in vivo or ex vivo administration protocol. The preferred routes of administration will be apparent to those of skill in the art, depending on the type of condition to be prevented or treated; whether the composition is nucleic acid based, protein based, or cell based; and/or the target cell/tissue. For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for deliver to mucosal tissues include, bronchial, intradermal, intramuscular, intranasal, other inhalatory, rectal, subcutaneous, topical, transdermal, vaginal and urethral routes. Combinations of routes of delivery can be used and in some instances, may enhance the therapeutic effects of the composition.

Ex vivo administration refers to performing part of the regulatory step outside of the patient, such as administering a composition (nucleic acid or protein) of the present invention to a population of cells removed from a patient under conditions such that the composition contacts and/or enters the cell, and returning the cells to the patient. Ex vivo methods are particularly suitable when the target cell type can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety. Although a specific example may not directly apply to the administration of a CBS-encoding nucleic acid molecule of the invention, the purpose of the examples is to demonstrate the gene therapy techniques have been successfully used prior to the present invention.

For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811: 299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many to examples, retroviral vector; Blaese et al., 1995, *Science* 270:475-480; Bordignon et al., 1995, *Science* 270:470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al. (1999, *J. Clin. Invest.* 104:21-29) demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J. Nutr. Sci. Vitaminol.* 44:569-572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865-869). As discussed above, Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector which is deficient for the immediate early genes, ICP4, 22 and 27, to deliver and express two different receptors in synovial lining cells in vivo (Oligino et al., 1999, *Gene Ther.* 6:1713-1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701-709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J. Immunol.* 160:5213-5220). In another study, murine leukemia virus-based retroviral vector was used to deliver (by intraarticular injection) and express a human growth hormone gene both ex vivo and in vivo (Ghivizzani et al., 1997, *Gene Ther.* 4:977-982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid. Finally, it is noted that ex ViVO gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230-234). Therefore, the state of the art in gene therapy has led the FDA to consider human gene therapy an appropriate strategy for the treatment of at least arthritis. Taken together, all of the above studies in gene therapy indicate that delivery and expression of a recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include an isolated nucleic acid molecule of the present invention, and preferably includes a recombinant molecule of the present invention that preferably is replication, or otherwise amplification, competent. A naked nucleic acid reagent of the present invention can comprise one or more nucleic acid molecules of the present invention including a dicistronic recombinant molecule. Naked nucleic acid delivery can include intramuscular, subcutaneous, intradermal, transdermal, intranasal and oral routes of administration, with direct injection into the target tissue being most preferred. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 μm in diameter) and are propelled into skin cells or muscle with a "gene gun."

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred patients to protect include humans.

One embodiment of the invention relates to the use of a CBS variant described herein or a nucleic acid encoding the same (including fragments and homologues), in an in vitro assay or production system to produce cystathionine or cysteine (in conjunction with cystathionine γ-lyase). For example, one can contact a CBS variant of the invention to a suitable substrate to utilize the enzymatic activity of the CBS protein. In another embodiment, CBS variants can also be used to remove or produce hydrogen sulfide. For example, removal of hydrogen sulfide is of concern in the production of beer. Any suitable production protocol can be used, and such methods are well known in the art. For example, the CBS variant can be bound to a solid support by a variety of methods including adsorption, cross-linking (including covalent bonding), and entrapment, and the enzyme is contacted with a substrate and other factors under suitable culture conditions. A solid support refers to any solid organic supports, artificial membranes, biopolymer supports, or inorganic supports that can form a bond with a CBS variant without significantly effecting the activity of the enzyme. Suitable culture conditions have been described above with regard to the production of recombinant CBS variants and in the Examples section. Products produced by a method of the present invention (e.g., cystathionine, cysteine) can be recovered by conventional methods and/or used in other methods.

Each reference described and/or cited herein is incorporated by reference in its entirety.

The following examples are provided for the purpose of illustration and are not intended to limit the scope of the present invention.

EXAMPLES

The following experimental procedures were used in the Examples below, unless otherwise stated.

Materials

Unless otherwise stated all materials were obtained from Sigma. L-[U-$^{14}$C] Serine was obtained from NEN Life Science products. Enhanced chemiluminescence reagents for Western blotting were purchased from Amersham-Pharmacia Biotech. Immobilon-P polyvinylidenefluoride membrane was purchased from Millipore.

Plasmids

With the exception of pKK Δ1-70 Δ401-551 and pGEX-6P-1 Δ1-70 Δ401-551, all of the C- and N-terminal deletion constructs used in this study were generated by a modification of the previously described pHCS3 CBS expression construct (Kozich and Kraus, 1992, *Hum. Mutat.* 1, 113-123) which contains the CBS full-length coding sequence (SEQ ID NO:1) cloned into pKK388.1. In this construct, CBS expression is governed by the IPTG inducible tac promoter. To generate all C-terminal deletion constructs, CBS cDNA fragments spanning the desired nucleotide residues (Table I) were amplified using primers incorporating Sph I and Kpn I sites to the 5' and 3' respective ends of the PCR product. All PCR products were then cut with Sph I and Kpn I and cloned by ligation into the pHCS3 vector digested with Sph I and Kpn I. Expression constructs pKK Δ1-39 and pKK Δ1-70 were generated by PCR-amplification of the CBS cDNA regions encoding amino acids 40-336 and 71-336 of SEQ ID NO:2, respectively. For both of these N-terminal deletion mutants, the sense primer was used to introduce an Nco I site to the 5' end of the amplified product (Table I). An Sph I site naturally occurs in the CBS cDNA, just upstream of the antisense primer hybridization site (base pare position 1012, according to the CBS cDNA numbering, ref. 25). PCR products thus generated were then digested with Nco I and Sph I and ligated into the pHCS3 plasmid cut with the same enzymes.

TABLE 1

| Construct | PCR primers used for insert amplification | | | | Amplified CBS cDNA region [bp] |
|---|---|---|---|---|---|
| | Sense | Restriction site | Antisense | Restriction site | |
| pKK CBS Δ551[a] | 126 | Sph I | 285 | Kpn I | 1010-1650 |
| pKK CBS Δ544-551[a] | 126 | Sph I | 355 | Kpn I | 1010-1029 |
| pKK CBS Δ534-551[a] | 126 | Sph I | 284 | Kpn I | 1010-1599 |
| pKK CBS Δ524-551[a] | 126 | Sph I | 257 | Kpn I | 1010-1569 |
| pKK CBS Δ497-551[a] | 126 | Sph I | 256 | Kpn I | 1010-1488 |
| pKK CBS Δ488-551[a] | 126 | Sph I | 210 | Kpn I | 1010-1464 |
| pKK CBS Δ442-551[a] | 126 | Sph I | 216 | Kpn I | 1010-1323 |
| pKK CBS Δ414-551[a] | 126 | Sph I | 283 | Kpn I | 1010-1239 |
| pKK CBS Δ1-39[a] | 389 | NcoI | 127 | None | 120-1010 |
| pKK CBS Δ1-70[a] | 384 | NcoI | 127 | None | 213-1010 |
| pKK CBS Δ1-70 Δ401-551[b] | 384 | NcoI | 378 | XhoI | 213-1200 |
| pGEX-6P-1 CBS Δ1-70 Δ401-551[c] | 377 | ApaI | 378 | XhoI | 213-1200 |

| Primer | Primer sequence[d] |
|---|---|
| 126 [SEQ ID NO: 3] | CGTAGAATTCACCTTTGCCC<u>GCATGC</u>TGAT |
| 127 [SEQ ID NO: 4] | TACGATCGATGGCCCTCCTGCAGCTCCTGCGC |
| 210 [SEQ ID NO: 5] | TACG<u>GGTACC</u>TCATTTGAACTGCTTGTAGATGAC |

TABLE 1-continued

| | | |
|---|---|---|
| 216 | [SEQ ID NO: 6] | TACGGGTACCTCACTTCTCCCGGAGGAGCGCGAT |
| 256 | [SEQ ID NO: 7] | TACGGGTACCTCACAGCGTGTCCGTGAGGCGGATC |
| 257 | [SEQ ID NO: 8] | TACGGGTACCTCACTTCCCGGTGCTGTGGTACTGG |
| 283 | [SEQ ID NO: 9] | TACGGGTACCTCAACGGAGGTGCCACCACCAGGGC |
| 284 | [SEQ ID NO: 10] | TACGGGTACCTCACACCCCGAACACCATCTGCCGC |
| 285 | [SEQ ID NO: 11] | TACGGGTACCTCACTGGTCCCGCTCCTGGGCGGCC |
| 355 | [SEQ ID NO: 12] | TACGGGTACCTCACACGAAGTTCAGCAAGT |
| 377 | [SEQ ID NO: 13] | TCAGCTAGGGCCCGCAAAATCTCCAAAAATCTTGCCA |
| 378 | [SEQ ID NO: 14] | ACCGCTCGAGTCACTCCTCCTTCAGAAAGCC |
| 384 | [SEQ ID NO: 15] | TACGCCATGGGGCCCGCAAAATCTCCAAAAATC |
| 389 | [SEQ ID NO: 16] | TACGCCATGGAGCCCCTGTGGATCCGGCCC |

To make the pKK Δ1-70 Δ401-551 construct, the relevant portion of the CBS coding sequence was amplified by PCR using a sense primer carrying an Nco I site at the 5' end of the primer and an appropriately designed antisense primer without any additional restriction site. The PCR product encompassing the relevant nucleotides (Table I) was then cut with Nco I; the 3' end of the PCR product remained blunt. This PCR fragment was then ligated into pKK388.1 digested with Nco I and Sma I.

In order to generate the pGEX-6P-1 Δ1-70 Δ401-551 glutathione S-transferase (GST) fusion expression construct, the pGEX-6P-1 vector internal Apa I site was abolished by site-directed mutagenesis of nucleotide 3893 from a C to a T. Subsequently, the CBS cDNA region encoding amino acid residues 71-400 (of SEQ ID NO:2) was amplified using primers incorporating Apa I and Xho I sites to the 5' and 3' respective ends of the PCR product. Both the PCR product and the modified pGEX-6P-1 vector were cut with Apa I and Xho I and ligated together.

Finally, all constructs were transformed into E. coli BL21 (Stratagene). The authenticity of all constructs was verified by DNA sequencing using a Thermo Sequenase Cy5.5 sequencing kit (Amersham Pharmacia Biotech) and the Visible Genetics Long-Read Tower System-V3.1 DNA sequencer according to the manufacturer's instructions.

Bacterial Expression Analysis of CBS Deletion Mutants

Growth of E. coli BL21 cells bearing the CBS mutant constructs, induction of expression and the generation of crude cell lysates were performed as described previously (Maclean et al., 2002, Hum. Mutat. 19(6), 641-55). The insoluble fraction was prepared as follows: after the centrifugation of the sonicated homogenate, pelleted cell debris were thoroughly washed with chilled 1× Tris-buffered saline, pH 8.0. The pellets were then resuspended in 1 ml of the lysis buffer (Maclean et al., ibid.) followed by a brief sonication in order to homogenize the insoluble fraction.

CBS Activity Assay

CBS activity was determined by a previously described radioisotope assay using [$^{14}$C] serine as the labeled substrate (Kraus, 1987, Methods Enzymol. 143, 388-394). Protein concentrations were determined by the Lowry procedure (Lowry et al., 1951, J. Biol. Chem. 193, 265-275) using bovine serum albumin (BSA) as a standard. One unit of activity is defined as the amount of CBS that catalyzes the formation of 1 μmol of cystathionine in 1 h at 37° C.

Denaturing and Native Polyacrylamide Gel Electrophoresis and Western Blotting

Western blot analysis of crude cell lysates under both denaturing and native conditions was performed as described previously (Janosik, 2001, supra) with some modifications. Soluble fractions of E. coli lysates containing the expressed mutant proteins were mixed with sample buffer and run on a 6% native PAGE without a stacking gel. The final composition of the sample buffer was: 50 mM Tris-HCl, pH 8.9, 1 mM DTT, 10% glycerol, 0.001% bromphenol blue. Detection of heme was performed using a previously described method that relies on heme peroxidase activity (Vargas et al., 1993, Anal. Biochem. 209(2), 323-6).

Densitometric Scanning Analysis

Quantitative densitometry analysis was performed using the Imagemaster 1D (version 2.0) software (Pharmacia). To construct a calibration curve, 50, 75, 100, 250, 500 and 1000 ng of purified wild type CBS protein were run on an SDS-PAGE together with crude cell lysates of the individual mutants. Following electrophoresis, Western blot immunoanalysis was conducted using rabbit anti-CBS serum. The signals corresponding to the experimentally observed CBS mutant subunits were all within the linear range of the calibration curve constructed with purified human CBS.

EXAMPLE 1

The following example describes the expression analysis of the human CBS deletion mutants in E. coli.

Unlike the well-conserved catalytic core, both the ~70 amino acid N-terminal and ~150 amino acid C-terminal regions of human CBS do not share any homology with CS and CBS enzymes from other organisms (FIG. 1). Referring to FIG. 1, the double deletion mutant is included in the scheme to illustrate the near identity of the Δ1-70 Δ401-551 (referring to SEQ ID NO:2) human truncated CBS species to CS enzymes. Filled boxes represent conserved domains, flat lines denote non-conserved regions. The area designated "CBS/CS" represents a highly conserved region present in both CBS and CS enzymes; this region also displays significant structural conservation with several other members of the family of the PLP-dependent enzymes such as serine/threonine deaminases and β subunit of tryptophan to synthase (Meier et al., 2001, Embo J. 20(15), 3910-6). In human CBS, this region comprises residues 84-382. The CBS domain is ~55 amino acid domain of an unknown function, which is found in a wide variety of otherwise, unrelated proteins (Bateman, 1997 Trends Biochem. Sci. 22, 12-13). Two copies of this motif are present in the C-terminal regions of both human and yeast CBS. The approximate position of the heme binding in the human CBS enzyme (Cys52, His65) is marked with an asterisk. CBS HS, Homo sapiens (Swiss-Prot # P35520); CBS SC, Saccharomyces cerevisiae (Swiss-Prot # P32582); CBS TC, Trypanosoma cruzi (Swiss-Prot # Q9BH24); CS ST, Salmonella typhimurium, (Swiss-Prot # P12674); CBS DD, human CBS Δ1-70 Δ401-551 deletion mutant.

Figure 2:
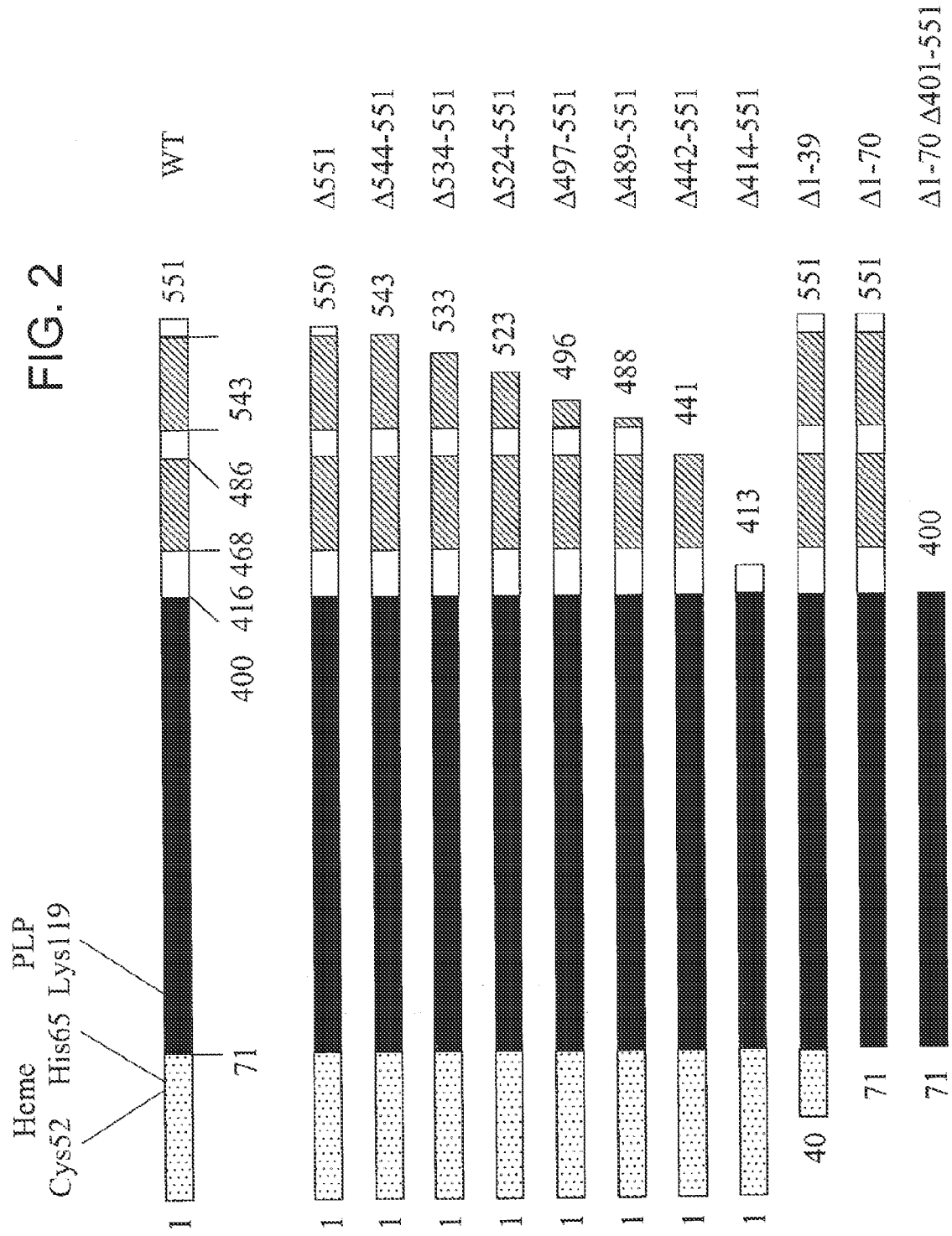
FIG. 2 is a schematic drawing showing the wild-type and truncated forms of human CBS described in the Examples.

A series of human CBS deletion mutants lacking various portions of these non-conserved regions were constructed (FIG. 2) and over-expressed using the present inventors' previously described E. coli based expression system (Kozich and Kraus, 1992, supra). In this system, CBS is expressed without any fusion partner under the control of the tac promoter. Referring to FIG. 2, the solid black box denotes the catalytic core (according to the present invention) of human CBS, spanning amino acid residues 71-400 (SEQ ID NO:2, described for the first time herein). The white box represents the C-terminal regulatory region. The two "CBS domain" motifs (CBS1 and CBS2) located within the C-terminal regulatory region are shown as crosshatched boxes. A dotted box indicates the 70 amino acid N-terminal domain, which houses the heme ligand. Numbers located at the beginning and end of each domain indicate the amino acid residue position. The positions of the two heme-binding residues, Cys52 and His65 (Meier et al., 2001, supra) and the PLP binding Lys119 (Kery et al., 1999, *Biochemistry* 38(9), 2716-24) are indicated.

Figure 3:
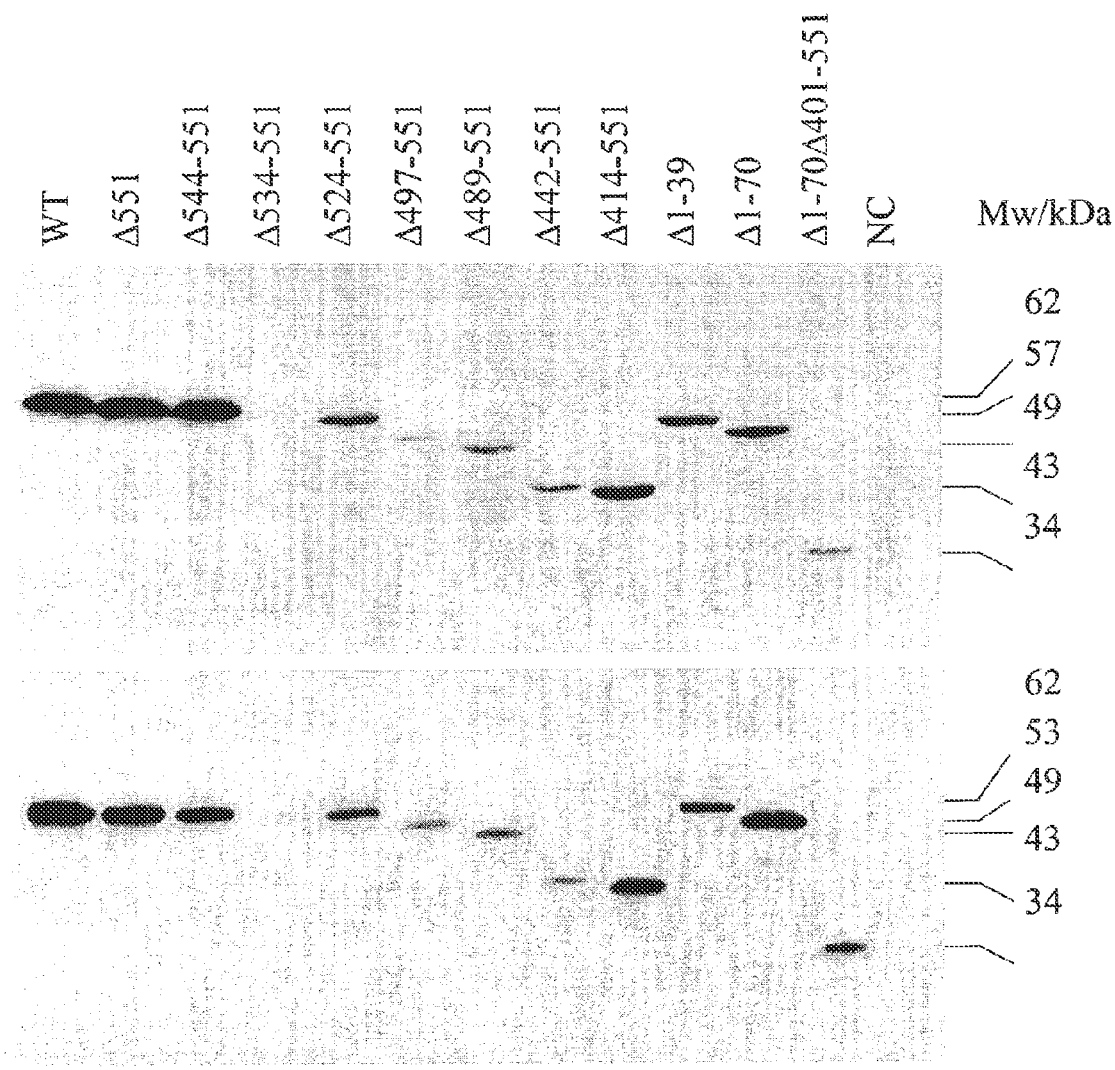
FIG. 3 is a digitized image of a Western blot showing an analysis of wild type CBS and N- and C-terminal deletion mutants in *E. coli* crude extracts.

Both soluble and insoluble fractions of the bacterial lysates were analyzed by Western blotting using a CBS-specific antisera. Referring to FIG. 3, 75 μg of total protein from soluble (top) or insoluble (bottom) fractions were loaded on 9% SDS-polyacrylamide gel. After the electrophoresis, separated proteins were transferred onto a PVDF membrane and probed with affinity-purified CBS antibody. NC stands for negative control (*E. coli* cells containing no expression plasmid). Apparent molecular weights of the mutant CBS proteins were calculated from the logarithmic plot of Kaleidoscope broad range pre-stained molecular weight marker (Bio-Rad).

Analysis of the soluble fractions revealed significant differences in the observed levels of the individual CBS mutant subunits in *E. coli* lysates (FIG. 3, top). The relative amounts of both N-terminal deletion mutants (Δ1-39 and Δ1-70) were decreased several fold compared to that of the wild type control, indicating that deletion of these regions has a negative impact upon the level of the resultant CBS present in the soluble fraction. The observed protein levels of the deletion mutants lacking either one or eight C-terminal amino acid residues were comparable to that of the wild type control, but only traces of the Δ534-551 mutant subunits were detected in the soluble fraction. More extensive deletions from the C-terminus (mutants Δ524-551, Δ497-551, Δ489-551, Δ442-551 and Δ414-551) lead to a pronounced decrease in the amount of detectable CBS mutant subunits compared to the wild type control. Although diminished relative to the wild type control, it can be seen that the Δ414-551 construct, which lacks the entire C-terminal regulatory region, is present in a significantly higher concentration than the preceding deletion clones that lack between 18 and 109 C-terminal residues. Taken together, these findings indicate that partial deletions of the CBS C-terminal regulatory region that extend into and past the CBS2 domain are considerably more deleterious than removal of this entire region. The relative amount of the double deletion mutant (Δ1-70 Δ401-551) was also severely diminished, indicating that removal of these relatively large areas of the CBS protein compromises the ability of the protein to assemble correctly.

The reduced levels of some of the deletion mutant forms of CBS in the *E. coli* soluble fractions poses a question regarding the possible influence of these truncations upon the solubility of the resultant mutant forms of CBS. In the past, the present inventors have repeatedly observed that during the expression of wild type CBS in *E. coli*, a significant portion of the protein is produced as insoluble aggregates (unpublished results). Full-length wild type CBS also exhibits a strong tendency towards aggregation during the course of purification, as well as in the purified state, although this tendency is somewhat ameliorated by removal of the C-terminal regulatory region (Kery et al., 1998, supra; Janosik et al., 2001, *Acta Crystallogr. D Biol. Crystallogr.* 57(Pt 2), 289-291). In order to examine the possible effects of the various deletions upon CBS solubility, aliquots of the insoluble cell fractions obtained from the *E. coli* expression analysis described above were examined by Western blotting (FIG. 3, bottom). With two exceptions, the insoluble fractions were found to contain roughly the same amounts of the various CBS mutant proteins as the soluble fractions. Notably, both of the deletion mutants that lack the heme cofactor due to the absence of the Cys52 and His65 residues (Δ1-70 and Δ1-70 Δ401-551), and whose amounts were severely diminished in the soluble fraction, were approximately 5-fold more abundant in the insoluble fractions. It appears that the removal of the N-terminal region acts to decrease the solubility of these mutant forms of CBS and that this is responsible for the diminished amounts of these proteins in the soluble fractions. The Δ534-551 truncated protein was absent in both soluble and insoluble fractions, indicating that this deletion exerts a completely destructive effect upon CBS.

EXAMPLE 2

The following example shows the effects of truncations on CBS activity.

Relative enzyme activities were determined for all of the various deletion mutants by assaying crude cell lysate soluble fractions for CBS activity in the presence and absence of 1 mM AdoMet. The activities were normalized to the amounts of expressed CBS protein as determined by the densitometric scanning analysis of a Western blot of the cell lysate soluble fractions. Specific activities of all deletion mutants were expressed as a percentage of the wild type activity determined in the absence of AdoMet, which was considered to be 100% (Table II). The calculated specific activity for the wild type enzyme derived from this analysis was 213±19 U/mg which is strikingly consistent with the value of 220 U/mg that was determined previously for the purified recombinant wild enzyme (Kery et al., 1998, supra).

TABLE 2

| CBS mutant | Relative activity [%] | AdoMet activation [x-fold] | Oligomeric status | Heme binding |
|---|---|---|---|---|
| WT, 1-551 | 100 ± 0 | 4.42 ± 0.10 | 4-mer | yes |
| Δ551 | 99 ± 3 | 3.44 ± 0.12 | 4-mer | yes |
| Δ544-551 | 136 ± 13 | NA[a] | 4-mer | yes |
| Δ534-551 | 0 ± 0 | NA | ND[b] | ND |
| Δ524-551 | 30 ± 4 | NA | ND | ND |
| Δ497-551 | 292 ± 45 | NA | 2-mer | yes |
| Δ489-551 | 334 ± 61 | NA | 2-mer | yes |
| Δ442-551 | 264 ± 48 | NA | 2-mer | yes |
| Δ414-551 | 505 ± 62 | NA | 2-mer | yes |
| Δ1-39 | 52 ± 2 | 3.99 ± 0.12 | 4-mer | yes |
| Δ1-70 | 19 ± 2 | NA | 4-mer | no |
| Δ1-70 Δ401-551 | 2 ± 3 | NA | 2-mer | no |

[a]Not activated.
[b]Not detected due to degradation or aggregation.

While having no effect on the enzyme response to AdoMet, deletion of the non-conserved 39 amino acid N-terminal domain causes a 2-fold decrease of specific activity (Table II). Even though this mutant form of CBS was still induced nearly 4-fold by AdoMet, the scale of the impairment of CBS activity was conserved indicating that the absence of this sequence confers an intrinsic catalytic deficiency. Previous work has shown that this deficiency is not present when this domain is removed after the protein has been assembled (Kery et al., 1998, supra) indicating that this region plays an important role in ensuring the correct folding of the enzyme.

The effect of deleting the first 70 residues from the CBS N-terminal region was particularly interesting, as this region includes the heme-binding residues. Despite the fact that the resulting truncation mutant lacked the heme cofactor, it retained 20% of wild type activity. Interestingly, although still catalytically active, this mutant is AdoMet non-responsive, indicating that this region may play a role in the conformational response of the autoinhibitory C-terminal domain to AdoMet.

The removal of the C-terminal lysine (mutant Δ551) had no effect on either specific activity or the scale of AdoMet activation observed. However, the relatively subtle deletion of the last 8 C-terminal amino acids (mutant Δ544-551) caused a small constitutive activation of enzyme activity (36% higher than uninduced wild type) while rendering the enzyme immune to further activation by AdoMet. In terms of the location of the CBS domains, the deletion of these 8 C-terminal residues removed the non-conserved region downstream of the CBS2 domain (FIG. 1). Larger C-terminal deletions that involved the removal of significant portions of the CBS2 domain (mutants Δ534-551 and Δ524-551) resulted in a dramatic decrease in specific activity, which could not be further elevated by the addition of AdoMet. By extending the deletions up to amino acid 442, the truncations gradually removed up to half of the CBS 1 motif. All of these mutants were constitutively activated by ~3-fold (Table II). The mutant Δ414-551, lacking both of the proposed CBS1 and CBS2 domains, was ~5-fold more active then the wild type enzyme control in the absence of AdoMet. None of these constitutively activated deletion mutants could be further activated by AdoMet. These findings are consistent with the proposed autoinhibitory function of the C-terminal domain and the present inventors' data described above, regarding the effect of partial deletion of the C-terminal region upon CBS protein stability. The double deletion mutant, missing both 70 N-terminal amino acids and the entire C-terminal regulatory region was essentially inactive according to in vitro assay standards, with activity values as low as 2% of that of the wild type control. This heme-free mutant CBS enzyme was also found to be AdoMet non-responsive.

EXAMPLE 3

The following example describes the effect of truncations on the oligomeric status of CBS.

Previous work from the present inventors' laboratory and others has indicated that the region responsible for the assembly of CBS subunits into tetramers is located in the C-terminal region of CBS (Kery et al., 1998, supra; Shan et al., 1998, *Nat. Genet.* 19, 91-93). Recently, work from another group has suggested that the formation of CBS tetramers may involve residues outside of the C-terminal domain (Nozaki et al., 2001, supra). The series of deletion mutants generated in this present study provided the inventors with a useful tool to further delineate the region(s) of CBS associated with the formation of tetramers. In order to determine the oligomeric status of all of the present deletion mutants, soluble fractions of cell extracts were analyzed by native PAGE followed by Western blotting (results not is shown). A cell lysate derived from *E. coli* containing no expression plasmid was used as a negative control. The results indicated that deletion of the N-terminal 70 amino acids did not affect the oligomeric status of the enzyme. Similarly, the removal of either one or eight amino acids from the C-terminus was accompanied by the normal formation of tetrameric CBS. Investigation of the oligomeric status of the two subsequent deletion mutants (Δ534-551 and Δ524-551) was complicated by the degradation of the former and aggregation of the latter. However, the properties of the enzyme improved as larger regions of the C-terminal regulatory region were removed. All of the mutants missing between 55 and 138 amino acids from the C-terminus assemble into dimers, whose stability seems to increase with the extent of the deletion. The deletion mutant lacking the 70 N-terminal residues and the 151 amino acid C-terminal regulatory region also forms dimers. The present inventors' finding that removal of 70 N-terminal residues did not convert the enzyme from a tetramer to a dimer indicates that the residues associated with tetramer formation reside exclusively in the C-terminal region and are located between residues 497 and 543.

EXAMPLE 4

The following example describes the effect of truncations on the heme content.

In order to determine whether any of the deletions impaired heme binding, soluble fractions of cell extracts were run on a native polyacrylamide gel and analyzed by Western blotting. The blot was stained for the presence of heme (Vargas et al., 1993, *Anal. Biochem.* 209(2), 323-6) using a method relying on heme peroxidase activity (results not shown). As a negative control, lysate from *E. coli* containing no expression plasmid was used. The experiment demonstrated that all of the C-terminal deletion mutants, with the exception of those that were undetectable on the denaturing Western blot, were capable of binding the heme cofactor. The level of heme staining correlated well with the amount of CBS protein detected in the soluble fraction indicating that there has been no obvious change in the ability of the stable deletion mutants to bind and retain heme. The N-terminal deletion mutant Δ1-39 also contained heme. As expected, both mutants that had the heme binding residues deleted (Δ1-70 and Δ1-70 Δ401-551) completely lacked this cofactor.

EXAMPLE 5

The following example describes the expression of the Δ1-70 Δ401-551 CBS deletion mutant as a GST fusion protein.

Analysis of the Δ1-39 and Δ1-70 N-terminal mutants indicated that these mutant forms of CBS were decreased in terms of their relative stability and activity. As removal of a further 150 C-terminal residues is likely to augment this instability, the observed inactivity of the Δ1-70 Δ401-551 mutant is not surprising. However, as previous work (Kery et al., 1998, *Arch. Biochem. Biophys.* 355, 222-232) has shown that the removal of the 39 N-terminal and 138 C-terminal residues from full-length CBS does not diminish the resultant protein's activity, it appears that these domains are only required during the folding and assembly of the protein. Consequently, it is conceivable that stabilization of residues 71-400 during the folding and assembly process could lead to catalytically active CBS protein. In an effort to further delineate the catalytic region of CBS, the Δ1-70 Δ401-551 CBS deletion mutant was expressed as a fusion protein with the GST affinity tag at the N-terminus. The activity of this mutant was measured in the soluble fraction of a crude cell lysate, both in the presence and absence of 1 mM AdoMet. Surprisingly, and in direct contrast to the inventors' previous finding described above, this deletion mutant was found to be catalytically active when expressed as a GST fusion protein. When measured in the crude cell lysate, the activity of this deletion mutant was equivalent to 25% of that of the wild type enzyme. Although catalytically active, this mutant remained AdoMet non-responsive, which is consistent with the previous observation that the presence of the C-terminal regulatory region is required for AdoMet activation of the enzyme.

The GST tag enabled the rapid purification of large amounts of the Δ1-70 Δ401-551 CBS deletion mutant in a two-step procedure. The GST Δ1-70 Δ401-551 CBS fusion protein was purified from bacterial lysate by affinity chromatography using Glutathione Sepharose 4B. The GST tag was then released from the fusion protein by cleavage with PreScission™ protease. Due to an uncharacterized interaction between the cleaved Δ1-70 Δ401-551 CBS and the GST tag, it was not possible to remove the affinity tag by applying the digest onto a secondary Glutathione Sepharose 4B column. Instead, the cleaved GST tag was separated on a Sephadex G-100 size exclusion column. The protein composition and the degree of purity after each step of the purification procedure were analyzed by SDS-PAGE (FIG. 4C, inset). From a total of 6 L of culture, 31 mg of the Δ1-70 Δ401-551 CBS protein were obtained at ~95% purity with an overall yield of 28%. After removal of the GST tag, the purified Δ1-70 Δ401-551 CBS mutant exhibits 15% of the activity typically observed for the wild type enzyme. This result indicates that although CBS does not tolerate well the combined absence of the N-terminal 70 residues and the C-terminal domain during the folding and/or assembly process, these regions are not essential for catalysis once the protein has folded and assembled.

In order to determine the degree of PLP saturation, the Δ1-70 Δ401-551 CBS activity was measured in the presence and absence of this cofactor. The activity of the wild type is enzyme, fully saturated with this cofactor, does not increase in the presence of additional PLP. In contrast, the activity of the truncation mutant increased from 7.3 to 32.1 U/mg protein upon the addition of PLP to the assay mixture at a final concentration of 0.5 mM. Based on this result, the degree of enzyme saturation with PLP appears to be only 23%. Since the enzyme is kept in 50 µM PLP throughout the purification procedure, it is likely that the loss of PLP occurs when the enzyme is diluted upon addition to the activity assay mixture. Consequently, it appears that in common with yeast CBS (Taoka et al., 1999, *Biochemistry* 38(40), 13155-61), the Δ1-70 Δ401-551 deletion mutant has decreased affinity for PLP relative to the wild type form of CBS.

Figure 4A:
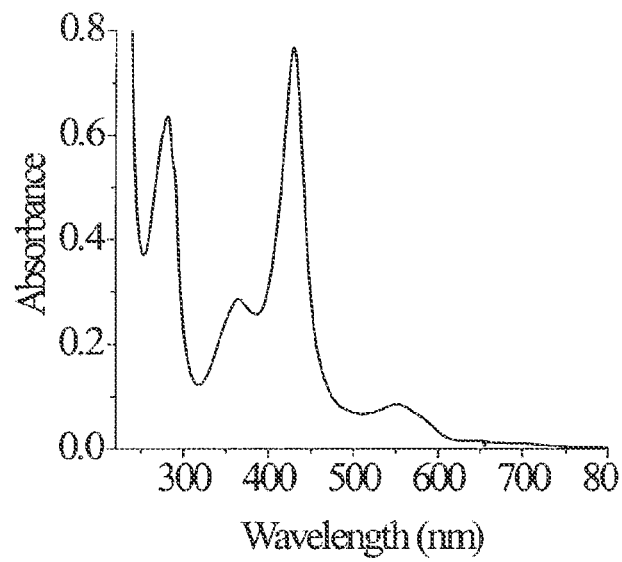
FIG. 4A is a graph showing the spectroscopic properties of purified human wild type CBS.
Figure 4B:
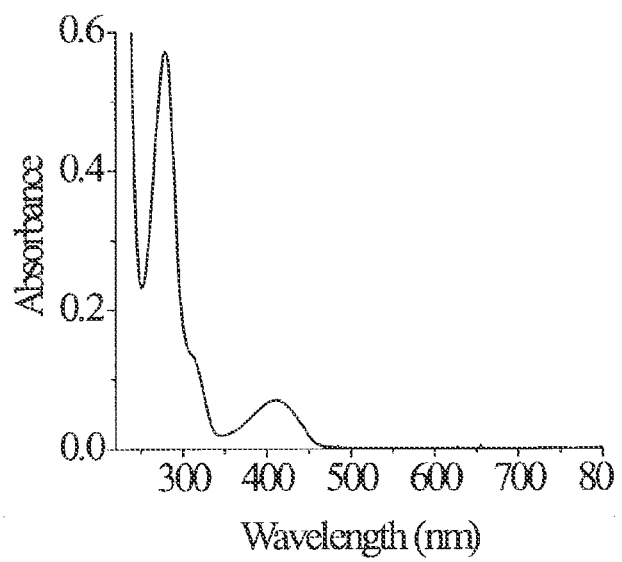
FIG. 4B is a graph showing the spectroscopic properties of yeast CBS.
Figure 4C:
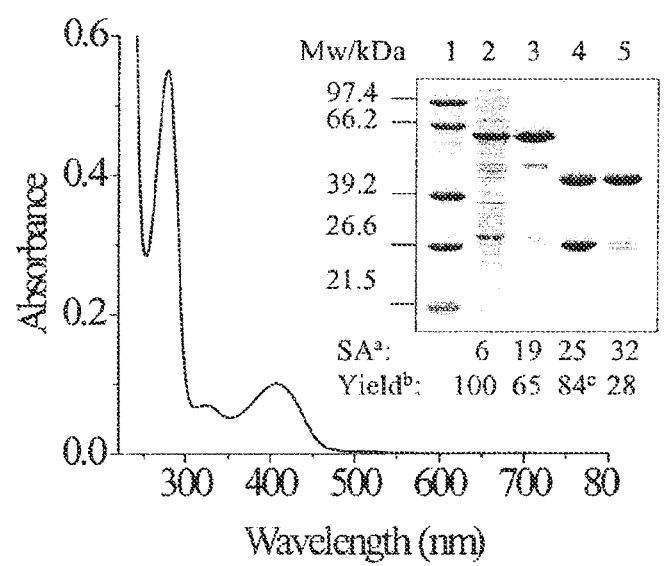
FIG. 4C is a graph showing the spectroscopic properties of the Δ1-70 Δ401-551 human CBS deletion mutant.

FIGS. 4A-4C show the absorption spectrum of the truncated enzyme (FIG. 4C) compared to that of the wild type human (FIG. 4A) and yeast (FIG. 4B) enzymes. Referring to FIGS. 4A-4C, UV-vis absorption spectra of all three enzymes (>95% purity in all cases) were recorded on a Hewlett-Packard diode array spectrophotometer (model 8453 UV-vis) in 0.1 M Na-acetate buffer, pH 7.4 at 25° C. All enzymes were pre-saturated with 50 µM PLP. The unbound PLP was then removed on a Bio-Spin 6 Column (Bio-Rad). The concentration of all proteins examined was adjusted to 0.7 mg/ml. The inset (C) illustrates the purification of the Δ1-70 Δ401-551 CBS deletion mutant. The expression and purification of the Δ1-70 Δ401-551 CBS deletion mutant was performed as described (Janosik et al., 2001, *Am. J. Hum. Genet.* 68(6), 1506-13) with some modifications. To improve the folding and solubility of the mutant protein, the expression was performed at 30° C. After cell lysis, the soluble fraction was incubated for 10 minutes at room temperature in the presence of 2 mM ATP and 10 mM $MgSO_4$ to prevent any non-specific interaction between the *E. coli* 70 kDa DNA K protein and the affinity resin. Isolated GST Δ1-70 Δ401-551 fusion protein was cleaved with PreScission™ protease (Amersham Pharmacia Biotech) in 1× cleavage buffer (50 mM Tris-HCl pH 7.0, 150 mM NaCl, 1 mM EDTA, 1 mM DTT) at 5° C. for 12 hours at a final concentration of 0.5 U/mg of protein. The GST tag was subsequently removed by size exclusion chromatography on a Sephadex G-100 column equilibrated with 25 mM MOPS pH 7.5, 1 mM MT and 50 µM PLP. Ten µg of protein was loaded per lane, run on a 9% SDS-polyacrylamide gel and stained with Coomassie brilliant blue. Aliquots from each step were assayed for activity. Lanes: 1, molecular weight marker (Premixed Protein Molecular Weight Marker, low-range, Roche); 2, cell lysate soluble fraction; 3, eluate from the Glutathione Sepharose 4B affinity column; 4, PreScission™ protease digestion products; 5, eluate from gel filtration chromatography. [a]Specific activity and [b]percentage yield for each step are shown below the gel. [c]The increase in observed yield after proteolytic cleavage is caused by an increase in the specific activity of Δ1-70 Δ401-551 CBS.

The absorption spectrum of the deletion mutant (FIG. 4C) exhibited major peaks at 280 and 412 nm, closely resembling the absorbance profile of yeast CBS (17, 18). The ratio of the $A_{(280nm)}/A_{(412nm)}$ was determined as 1:0.18, which is somewhat greater than the one reported for yeast CBS (Jhee et al., 2000, *J. Biol. Chem.* 275(16), 11541-4; Miles, 1986, in *Pyridoxal Phosphate Chemical, Biochemical and Medical Aspects* (Dolphin et al., ed) Vol. Part B. Vol. 1, pp. 253-310, John Wiley and Sons, New York). The spectra of both enzymes lack the Soret peak at 428 nm, reflecting the absence of the heme cofactor (FIGS. 4B & 4C). Similar absorption spectra were observed for crystals of the CBS active core from which the heme cofactor had been removed by carbon monoxide (Bruno et al., 2001, *J. Biol. Chem.* 276(1), 16-19).

EXAMPLE 6

The following, non-limiting examples illustrate how the CBS-encoding sequence (including wild-type and variants) can be introduced into an expression vector that includes a rhinovirus 3C protease cleavage recognition sequence, to produce a protein with no more than one or two non-CBS amino acid residues at the N-terminus.

Production of a Recombinant, Full-Length CBS Protein

Details of the methods have been described above with regard to Examples 1-5 and are further described below. To prepare an expression vector suitable for use in the present invention, the commercially available pGEX-6P-1 vector (Amersham Pharmacia Biotech) was modified by destroying the internal Apa I site located at the base pair position 3890 of the pGEX-6P-1 vector. This has been done by site-directed mutagenesis, using a custom designed primer and a QuikChange Site-Directed Mutagenesis Kit (Stratagene) according to manufacturer instructions, whereby the nucleotide at position 3893 of the vector was substituted as follows C(3893)→(3893). The resulting vector is referred to herein as pGEX-6P-1 (3890 ApaI–). The nucleic acid sequence encoding a CBS protein or isoform thereof is then cloned into the second ApaI site present in the pGEX-6P-1 vector, which is upstream of the polylinker and actually encodes the last two amino acid residues of the human rhinovirus 3C protease recognition site. The present inventors employed a three-piece ligation approach. First, the pGEX-6P-1 (3890 ApaI–) vector was cut with Apa I and Sal I restriction endonucleases (Sal I is an exemplary site and corresponds to a site in the multiple cloning region for the vector—other sites may be used, depending on the vector and constructs). Second, two primers encoding the last two amino acids of the human rhinovirus 3C protease recognition site and the first 10 amino acids of the human CBS sequence to be expressed (including the HCBSΔ414-551 isoform) were designed. Those two primers were hybridized together to form a short fragment with Apa I/Apa I overhangs. Third, the cDNA portion of the pAX5-HCBS WT construct (pAX5-HCBS WT was described in Bukovska et al., 1994, *Protein Expr. Purif.* 5, 442-448 and is incorporated herein by reference in its entirety) coding for amino acid residues 11-551 (of SEQ ID NO:2) was cut out using Apa I and Sal I restriction endonucleases. Finally, the digested pGEX-6P-1 (3890 Apa I−) vector, the fragment consisting of the two hybridized primers and the CBS cDNA fragment cut out of the pAX5-HCBS WT vector were ligated together. The resulting expression construct is referred to herein as pGEX-6P-1 3890 ApaI(−) HCBS WT.

The resulting expression vector is used to transform a recombinant host cell (e.g., *E. coli*) and the fusion protein comprising the CBS protein as a fusion protein with a GST tag (according to this example), is produced. The GST Tag is cleavable using the human rhinovirus 3C protease (available as the PreScission™ GST fusion protein, Amersham Pharmacia Biotech). After cleavage with this protease, there will be no additional amino acids left at the N-terminus of the CBS enzyme, and the only difference between the wild-type enzyme as it occurs in vivo and the recombinant protein is the substitution of the initial Met for Gly. In vivo, the initial Met of the wild-type protein is cleaved off as a result of a post-translational modification. The method for production of the recombinant protein by the host cell is described in the Examples below and one particular method is described in U.S. Pat. No. 5,635,375, supra.

In this example, if the CBS coding sequence was the full-length, wild-type sequence, the recombinant protein will be a tetrameric full length protein, containing PLP and heme, and can be activated by AdoMet. This protein is active and binds well to the GST resin. This is the construct that the present inventors use for large-scale, wild-type, human soluble cystathionine β-synthase purification.

Production of a Recombinant CBS Variant Having a C-Terminal Deletion

In a second non-limiting example, a CBS isoform (homologue) was produced using the method of the present invention. The CBS isoform is a truncated version of wild-type CBS which is missing the 138 C-terminal amino acids. This protein forms dimers having increased CBS activity and contains PLP and heme, but it can not be further activated by AdoMet. The construct encoding this protein is referred to herein as pGEX-6P-1 3890 ApaI(−) HCBSΔ414-551.

In this example, the pGEX-6P-1 (3890 Apa I−) vector produced by the present inventors (described above) was again used to introduce the wild-type CBS coding sequence as described in Example 1 and form an expression construct pGEX-6P-1 3890 ApaI(−) HCBS WT. The resulting construct was cut with restriction enzymes SphI and SalI. This region was replaced with the same region that has been excised from a nucleic acid sequence encoding a deletion mutant of HCBS that is missing the C-terminal 138 amino acid residues (e.g., pAX5-HCBSΔ414-551) (pAX5-HCBS WT was described in Bukovska et al., 1994, *Protein Expr. Purif.* 5, 442-448 and is incorporated herein by reference in its entirety).

One can amplify a CBS cDNA fragment spanning the desired nucleotide residues using the wild-type template. The sense primer should contain one desired restriction site e.g., Sph I site at the 5' end. The antisense primer should introduce a second desired restriction site (e.g., Kpn I site) and a stop codon at the 3' end of the PCR product. PCR products can then be cut with the restriction enzymes (e.g., Sph I and Kpn I) and cloned into a vector digested with the same restriction enzymes. This general strategy can be used to create various C-terminal deletion mutants (isoforms) of CBS. To create isoforms with N-terminal deletions larger then 12 amino acids a PCR strategy can be used. The forward primer has to contain the Apa I site at its 5' end in order to recreate the last two amino acids of the human rhinovirus 3C protease recognition site and the desired new amino terminus of the truncated CBS isoform. The reverse primer should contain an Sph I site to facilitate cloning of the PCR fragment into the Apa I-Sph I cut pGEX-6P-1 3890 Apa I (−) HCBS WT casette. It will be apparent to those of skill in the art that the use of a variety of isoforms of CBS and restriction sites can be developed and incorporated into the novel expression strategy describe herein.

The expression vector containing the human CBS isoform is introduced into a host cell and the recombinant protein is expressed, purified and cleaved from its fusion partner as described above. The resulting recombinant CBS isoform protein is active and binds well to the GST resin. This is the construct can be used for large-scale, Δ414-551 HS CBS purification.

Production of a Recombinant CBS Variant Having N-Terminal & C-Terminal Deletions In a third non-limiting example, a CBS isoform (homologue) was produced using the method of the present invention. The CBS isoform is a truncated version of wild-type CBS which is missing the N-terminal 70 amino acids and the 150 C-terminal amino acids. This protein is about a 36 kDa protein and contains PLP, but does not contain heme. The protein can be produced in large quantities and has reduced CBS activity. This protein is not stimulated by AdoMet. The construct encoding this protein is referred to herein as pGEX-6P-1 3890 ApaI(−) HCBSΔN1-70 ΔC401-551.

In this example, the pGEX-6P-1 (3890 Apa I−) vector produced by the present inventors was again used. The CBS cDNA region coding for amino acid residues 71-400 was amplified from a wildtype CBS template using a sense primer carrying the Apa I site corresponding to the pGEX-6P-1 (3890 Apa I−) vector and an antisense primer carrying the Xho I site. Both the PCR product and the pGEX-6P-1 (3890 Apa I−) vector were cut with Apa I and Xho I restriction endonucleases and ligated together.

Alternatively, one could create the construct by introducing the deletions sequentially. For example, a first construct containing a CBS sequence encoding a CBS isoform having the N-terminal 70 amino acids deleted could be prepared, using the general techniques described in above for the Δ414-551 HS CBS protein. This construct could then be cut using restriction enzymes corresponding to a C-terminal region of the CBS protein and this section could be replaced with an insert prepared by digestion with the same enzymes of a PCR product containing the desired exact C-terminal deletion. It is noted that the amino acid residue at position 71 in the wild type human soluble CBS protein is Ala (71); however, after the digest with the human rhinovirus 3C protease, the Gly and Pro from the recognition site PreScission™ site will remain at the N-terminus. Therefore, the N-terminus of the expressed, purified and cleaved recombinant protein will contain a Gly and Pro at the N-terminus prior to the Ala. By coincidence, a Pro preceding Ala(71) is the actual 70th amino acid residue in the wild type human CBS sequence. As such, the resulting recombinant protein might technically be referred to as a ΔN1-69 HCBS isoform containing one additional amino acid residue (Gly) at the N-terminus.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated human cystathionine β-synthase (CBS) variant having CBS biological activity, said variant having an amino acid sequence spanning from a starting position of amino acid residue 40 of SEQ ID NO: 2 to an ending position of one of amino acid residues from 401-550 of SEQ ID NO: 2; wherein said isolated human cystathionine β-synthase variant catalyzes the formation of cystathionine.

2. The isolated human cystathionine β-synthase variant of claim 1, wherein said ending position is amino acid residue 550 of SEQ ID NO: 2.

3. The isolated human cystathionine β-synthase variant of claim 1, wherein said ending position is amino acid residue 413 of SEQ ID NO: 2.

4. The isolated human cystathionine β-synthase variant of claim 1, wherein said ending position is one of amino acid residues from 414-550 of SEQ ID NO: 2.

5. The isolated human cystathionine β-synthase variant of claim 1, wherein said variant is at least 95% identical to said amino acid sequence with a starting position of amino acid residue 40 to and ending position of amino acid residue 413 of SEQ ID NO: 2 or at least 95% identical to the amino acid sequence from amino acid residues 40-550 of SEQ ID NO: 2.

6. The isolated human cystathionine β-synthase variant of claim 1, wherein said variant comprises no more than one or two amino acid residues at the N-terminus that is not a residue of the naturally occurring human cystathionine β-synthase amino acid sequence.

7. An isolated fusion protein comprising the isolated human cystathionine β-synthase variant of claim 1, covalently linked to a heterologous protein sequence.

8. A method to treat homocystinuria, comprising administering to a patient the isolated cystathionine β-synthase variant of claim 1.

9. An isolated, recombinant human cystathionine β-synthase variant, wherein said human cystathionine β-synthase variant comprises a) an amino acid sequence spanning positions 40-551, or 40-413 of SEQ ID NO: 2; b) an amino acid sequence that is at least 95% identical to positions 40-551, or 40-413 of SEQ ID NO: 2; or c) an enzymatically active fragment of an amino acid sequence spanning positions 40-551, or 40-413 of SEQ ID NO: 2, wherein said fragment catalyzes the formation of cystathionine.

10. The isolated, recombinant human cystathionine β-synthase variant of claim 9, spanning positions 40-551 of SEQ ID NO: 2.

11. The isolated, recombinant human cystathionine β-synthase variant of claim 9, spanning positions 40-413 of SEQ ID NO: 2.

12. A pharmaceutical composition comprising the human cystathionine β-synthase (CBS) variant of claim 1.

13. A method for treating homocystinuria, comprising administering to a patient the isolated CBS variant of claim 7.

14. A method for treating homocystinuria, comprising administering to a patient the pharmaceutical composition of claim 12.

* * * * *

SEQUENCE LISTING

<160> NUMBER OF SEQ ID NOS: 22

<210> SEQ ID NO 1
<211> LENGTH: 1656
<212> TYPE: DNA
<213> ORGANISM: Homo sapiens
<220> FEATURE:
<221> NAME/KEY: CDS
<222> LOCATION: (1)..(1656)

<400> SEQUENCE: 1

| | | | | | | | | | | | | | | | | |
|---|---|---|---|---|---|---|---|---|---|---|---|---|---|---|---|---|
| atg | cct | tct | gag | acc | ccc | cag | gca | gaa | gtg | ggg | ccc | aca | ggc | tgc | ccc | 48 |
| Met | Pro | Ser | Glu | Thr | Pro | Gln | Ala | Glu | Val | Gly | Pro | Thr | Gly | Cys | Pro | |
| 1 | | | | 5 | | | | | 10 | | | | | 15 | | |

| cac | cgc | tca | ggg | cca | cac | tcg | gcg | aag | ggg | agc | ctg | gag | aag | ggg | tcc | 96 |
|---|---|---|---|---|---|---|---|---|---|---|---|---|---|---|---|---|
| His | Arg | Ser | Gly | Pro | His | Ser | Ala | Lys | Gly | Ser | Leu | Glu | Lys | Gly | Ser | |
| | | | 20 | | | | | 25 | | | | | 30 | | | |

| cca | gag | gat | aag | gaa | gcc | aag | gag | ccc | ctg | tgg | atc | cgg | ccc | gat | gct | 144 |
|---|---|---|---|---|---|---|---|---|---|---|---|---|---|---|---|---|
| Pro | Glu | Asp | Lys | Glu | Ala | Lys | Glu | Pro | Leu | Trp | Ile | Arg | Pro | Asp | Ala | |
| | | | | 35 | | | | | 40 | | | | | 45 | | |

| ccg | agc | agg | tgc | acc | tgg | cag | ctg | ggc | cgg | cct | gcc | tcc | gag | tcc | cca | 192 |
|---|---|---|---|---|---|---|---|---|---|---|---|---|---|---|---|---|
| Pro | Ser | Arg | Cys | Thr | Trp | Gln | Leu | Gly | Arg | Pro | Ala | Ser | Glu | Ser | Pro | |
| | 50 | | | | | 55 | | | | | 60 | | | | | |

| cat | cac | cac | act | gcc | ccg | gca | aaa | tct | cca | aaa | atc | ttg | cca | gat | att | 240 |
|---|---|---|---|---|---|---|---|---|---|---|---|---|---|---|---|---|
| His | His | His | Thr | Ala | Pro | Ala | Lys | Ser | Pro | Lys | Ile | Leu | Pro | Asp | Ile | |
| 65 | | | | | 70 | | | | | 75 | | | | | 80 | |

| ctg | aag | aaa | atc | ggg | gac | acc | cct | atg | gtc | aga | atc | aac | aag | att | ggg | 288 |
|---|---|---|---|---|---|---|---|---|---|---|---|---|---|---|---|---|
| Leu | Lys | Lys | Ile | Gly | Asp | Thr | Pro | Met | Val | Arg | Ile | Asn | Lys | Ile | Gly | |
| | | | | 85 | | | | | 90 | | | | | 95 | | |

| aag | aag | ttc | ggc | ctg | aag | tgt | gag | ctc | ttg | gcc | aag | tgt | gag | ttc | ttc | 336 |
|---|---|---|---|---|---|---|---|---|---|---|---|---|---|---|---|---|
| Lys | Lys | Phe | Gly | Leu | Lys | Cys | Glu | Leu | Leu | Ala | Lys | Cys | Glu | Phe | Phe | |
| | | | | 100 | | | | | 105 | | | | | 110 | | |

| aac | gcg | ggc | ggg | agc | gtg | aag | gac | cgc | atc | agc | ctg | cgg | atg | att | gag | 384 |
|---|---|---|---|---|---|---|---|---|---|---|---|---|---|---|---|---|
| Asn | Ala | Gly | Gly | Ser | Val | Lys | Asp | Arg | Ile | Ser | Leu | Arg | Met | Ile | Glu | |
| | | | 115 | | | | | 120 | | | | | 125 | | | |

| gat | gct | gag | cgc | gac | ggg | acg | ctg | aag | ccc | ggg | gac | acg | att | atc | gag | 432 |
|---|---|---|---|---|---|---|---|---|---|---|---|---|---|---|---|---|
| Asp | Ala | Glu | Arg | Asp | Gly | Thr | Leu | Lys | Pro | Gly | Asp | Thr | Ile | Ile | Glu | |
| | 130 | | | | | 135 | | | | | 140 | | | | | |

| ccg | aca | tcc | ggg | aac | acc | ggg | atc | ggg | ctg | gcc | ctg | gct | gcg | gca | gtg | 480 |
|---|---|---|---|---|---|---|---|---|---|---|---|---|---|---|---|---|
| Pro | Thr | Ser | Gly | Asn | Thr | Gly | Ile | Gly | Leu | Ala | Leu | Ala | Ala | Ala | Val | |
| 145 | | | | | 150 | | | | | 155 | | | | | 160 | |

| agg | ggc | tat | cgc | tgc | atc | atc | gtg | atg | cca | gag | aag | atg | agc | tcc | gag | 528 |
|---|---|---|---|---|---|---|---|---|---|---|---|---|---|---|---|---|
| Arg | Gly | Tyr | Arg | Cys | Ile | Ile | Val | Met | Pro | Glu | Lys | Met | Ser | Ser | Glu | |
| | | | | 165 | | | | | 170 | | | | | 175 | | |

| aag | gtg | gac | gtg | ctg | cgg | gca | ctg | ggg | gct | gag | att | gtg | agg | acg | ccc | 576 |
|---|---|---|---|---|---|---|---|---|---|---|---|---|---|---|---|---|
| Lys | Val | Asp | Val | Leu | Arg | Ala | Leu | Gly | Ala | Glu | Ile | Val | Arg | Thr | Pro | |
| | | | | 180 | | | | | 185 | | | | | 190 | | |

| acc | aat | gcc | agg | ttc | gac | tcc | ccg | gag | tca | cac | gtg | ggg | gtg | gcc | tgg | 624 |
|---|---|---|---|---|---|---|---|---|---|---|---|---|---|---|---|---|
| Thr | Asn | Ala | Arg | Phe | Asp | Ser | Pro | Glu | Ser | His | Val | Gly | Val | Ala | Trp | |
| | | | 195 | | | | | 200 | | | | | 205 | | | |

| cgg | ctg | aag | aac | gaa | atc | ccc | aat | tct | cac | atc | cta | gac | cag | tac | cgc | 672 |
|---|---|---|---|---|---|---|---|---|---|---|---|---|---|---|---|---|
| Arg | Leu | Lys | Asn | Glu | Ile | Pro | Asn | Ser | His | Ile | Leu | Asp | Gln | Tyr | Arg | |
| | 210 | | | | | 215 | | | | | 220 | | | | | |

| aac | gcc | agc | aac | ccc | ctg | gct | cac | tac | gac | acc | acc | gct | gat | gag | atc | 720 |
|---|---|---|---|---|---|---|---|---|---|---|---|---|---|---|---|---|
| Asn | Ala | Ser | Asn | Pro | Leu | Ala | His | Tyr | Asp | Thr | Thr | Ala | Asp | Glu | Ile | |
| 225 | | | | | 230 | | | | | 235 | | | | | 240 | |

| ctg | cag | cag | tgt | gat | ggg | aag | ctg | gac | atg | ctg | gtg | gct | tca | gtg | ggc | 768 |
|---|---|---|---|---|---|---|---|---|---|---|---|---|---|---|---|---|
| Leu | Gln | Gln | Cys | Asp | Gly | Lys | Leu | Asp | Met | Leu | Val | Ala | Ser | Val | Gly | |
| | | | | 245 | | | | | 250 | | | | | 255 | | |

| acg | ggc | ggc | acc | atc | acg | ggc | att | gcc | agg | aag | ctg | aag | gag | aag | tgt | 816 |
|---|---|---|---|---|---|---|---|---|---|---|---|---|---|---|---|---|
| Thr | Gly | Gly | Thr | Ile | Thr | Gly | Ile | Ala | Arg | Lys | Leu | Lys | Glu | Lys | Cys | |

```
           260                265                270
cct gga tgc agg atc att ggg gtg gat ccc gaa ggg tcc atc ctc gca      864
Pro Gly Cys Arg Ile Ile Gly Val Asp Pro Glu Gly Ser Ile Leu Ala
        275                280                285 gag ccg gag gag ctg aac cag acg gag cag aca acc tac gag gtg gaa      912
Glu Pro Glu Glu Leu Asn Gln Thr Glu Gln Thr Thr Tyr Glu Val Glu
    290                295                300 ggg atc ggc tac gac ttc atc ccc acg gtg ctg gac agg acg gtg gtg      960
Gly Ile Gly Tyr Asp Phe Ile Pro Thr Val Leu Asp Arg Thr Val Val
305                310                315                320 gac aag tgg ttc aag agc aac gat gag gag gcg ttc acc ttt gcc cgc     1008
Asp Lys Trp Phe Lys Ser Asn Asp Glu Glu Ala Phe Thr Phe Ala Arg
                325                330                335 atg ctg atc gcg caa gag ggg ctg ctg tgc ggt ggc agt gct ggc agc     1056
Met Leu Ile Ala Gln Glu Gly Leu Leu Cys Gly Gly Ser Ala Gly Ser
            340                345                350 acg gtg gcg gtg gcc gtg aag gct gcg cag gag ctg cag gag ggc cag     1104
Thr Val Ala Val Ala Val Lys Ala Ala Gln Glu Leu Gln Glu Gly Gln
        355                360                365 cgc tgc gtg gtc att ctg ccc gac tca gtg cgg aac tac atg acc aag     1152
Arg Cys Val Val Ile Leu Pro Asp Ser Val Arg Asn Tyr Met Thr Lys
    370                375                380 ttc ctg agc gac agg tgg atg ctg cag aag ggc ttt ctg aag gag gag     1200
Phe Leu Ser Asp Arg Trp Met Leu Gln Lys Gly Phe Leu Lys Glu Glu
385                390                395                400 gac ctc acg gag aag aag ccc tgg tgg tgg cac ctc cgt gtt cag gag     1248
Asp Leu Thr Glu Lys Lys Pro Trp Trp Trp His Leu Arg Val Gln Glu
                405                410                415 ctg ggc ctg tca gcc ccg ctg acc gtg ctc ccg acc atc acc tgt ggg     1296
Leu Gly Leu Ser Ala Pro Leu Thr Val Leu Pro Thr Ile Thr Cys Gly
            420                425                430 cac acc atc gag atc ctc cgg gag aag ggc ttc gac cag gcg ccc gtg     1344
His Thr Ile Glu Ile Leu Arg Glu Lys Gly Phe Asp Gln Ala Pro Val
        435                440                445 gtg gat gag gcg ggg gta atc ctg gga atg gtg acg ctt ggg aac atg     1392
Val Asp Glu Ala Gly Val Ile Leu Gly Met Val Thr Leu Gly Asn Met
    450                455                460 ctc tcg tcc ctg ctt gcc ggg aag gtg cag ccg tca gac caa gtt ggc     1440
Leu Ser Ser Leu Leu Ala Gly Lys Val Gln Pro Ser Asp Gln Val Gly
465                470                475                480 aaa gtc atc tac aag cag ttc aaa cag atc cgc ctc acg gac acg ctg     1488
Lys Val Ile Tyr Lys Gln Phe Lys Gln Ile Arg Leu Thr Asp Thr Leu
                485                490                495 ggc agg ctc tcg cac atc ctg gag atg gac cac ttc gcc ctg gtg gtg     1536
Gly Arg Leu Ser His Ile Leu Glu Met Asp His Phe Ala Leu Val Val
            500                505                510 cac gag cag atc cag tac cac agc acc ggg aag tcc agt cag cgg cag     1584
His Glu Gln Ile Gln Tyr His Ser Thr Gly Lys Ser Ser Gln Arg Gln
        515                520                525 atg gtg ttc ggg gtg gtc acc gcc att gac ttg ctg aac ttc gtg gcc     1632
Met Val Phe Gly Val Val Thr Ala Ile Asp Leu Leu Asn Phe Val Ala
    530                535                540 gcc cag gag cgg gac cag aag tga                                      1656
Ala Gln Glu Arg Asp Gln Lys
545                550

<210> SEQ ID NO 2
<211> LENGTH: 551
<212> TYPE: PRT
<213> ORGANISM: Homo sapiens
```

```
<400> SEQUENCE: 2

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
    50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
            115                 120                 125

Asp Ala Glu Arg Asp Gly Thr Leu Lys Pro Gly Asp Thr Ile Ile Glu
130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
    210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
            275                 280                 285

Glu Pro Glu Glu Leu Asn Gln Thr Glu Gln Thr Thr Tyr Glu Val Glu
        290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
            355                 360                 365

Arg Cys Val Val Ile Leu Pro Asp Ser Val Arg Asn Tyr Met Thr Lys
        370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg Val Gln Glu
```

```
                    405                 410                 415
Leu Gly Leu Ser Ala Pro Leu Thr Val Leu Pro Thr Ile Thr Cys Gly
            420                 425                 430

His Thr Ile Glu Ile Leu Arg Glu Lys Gly Phe Asp Gln Ala Pro Val
        435                 440                 445

Val Asp Glu Ala Gly Val Ile Leu Gly Met Val Thr Leu Gly Asn Met
    450                 455                 460

Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
                485                 490                 495

Gly Arg Leu Ser His Ile Leu Glu Met Asp His Phe Ala Leu Val Val
            500                 505                 510

His Glu Gln Ile Gln Tyr His Ser Thr Gly Lys Ser Ser Gln Arg Gln
        515                 520                 525

Met Val Phe Gly Val Val Thr Ala Ile Asp Leu Leu Asn Phe Val Ala
    530                 535                 540

Ala Gln Glu Arg Asp Gln Lys
545                 550

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
cgtagaattc acctttgccc gcatgctgat                                        30

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
tacgatcgat ggccctcctg cagctcctgc gc                                     32

<210> SEQ ID NO 5
<211> LENGTH: 34
<212> TYPE: DNA
<213> ORGANISM: Artificial Sequence
<220> FEATURE:
<223> OTHER INFORMATION: primer

<400> SEQUENCE: 5
tacgggtacc tcatttgaac tgcttgtaga tgac                                   34

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
tacgggtacc tcacttctcc cggaggagcg cgat                                   34

<210> SEQ ID NO 7
```

```
<211> LENGTH: 35
<212> TYPE: DNA
<213> ORGANISM: Artificial Sequence
<220> FEATURE:
<223> OTHER INFORMATION: primer

<400> SEQUENCE: 7
tacgggtacc tcacagcgtg tccgtgaggc ggatc                              35

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
tacgggtacc tcacttcccg gtgctgtggt actgg                              35

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
tacgggtacc tcaacggagg tgccaccacc agggc                              35

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
tacgggtacc tcacaccccg aacaccatct gccgc                              35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
tacgggtacc tcactggtcc cgctcctggg cggcc                              35

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
tacgggtacc tcacacgaag ttcagcaagt                                    30

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
```

```
tcagctaggg cccgcaaaat ctccaaaaat cttgccagat                              40
```

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14

```
accgctcgag tcactcctcc ttcagaaagc c                                      31
```

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15

```
tacgccatgg ggcccgcaaa atctccaaaa atc                                    33
```

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16

```
tacgccatgg agcccctgtg gatccggccc                                        30
```

<210> SEQ ID NO 17
<211> LENGTH: 8
<212> TYPE: PRT
<213> ORGANISM: Artificial sequence
<220> FEATURE:
<223> OTHER INFORMATION: peptide

<400> SEQUENCE: 17

```
Leu Glu Val Leu Phe Gln Gly Pro
1               5
```

<210> SEQ ID NO 18
<211> LENGTH: 522
<212> TYPE: PRT
<213> ORGANISM: Drosophila melanogaster

<400> SEQUENCE: 18

```
Met Pro Gln Pro Lys Pro Tyr Glu Arg Pro Ala Asp Phe Ile Asp Pro
1               5                   10                  15

Gly Lys Pro Ser Lys Cys Lys Trp His Leu Gly Thr Ala Glu Lys Ser
            20                  25                  30

Pro His Ile His Arg Gly Ile Ala His Arg Gln Gln Ile Thr Pro Asn
        35                  40                  45

Ile Leu Glu Val Ile Gly Cys Thr Pro Leu Val Lys Leu Asn Asn Ile
    50                  55                  60

Pro Ala Ser Asp Gly Ile Glu Cys Glu Met Tyr Ala Lys Cys Glu Phe
65                  70                  75                  80

Leu Asn Pro Gly Gly Ser Val Lys Asp Arg Ile Gly Tyr Arg Met Val
                85                  90                  95

Gln Asp Ala Glu Glu Gln Gly Leu Leu Lys Pro Gly Tyr Thr Ile Ile
```

```
            100                 105                 110
Glu Pro Thr Ser Gly Asn Thr Gly Ile Gly Leu Ala Met Ala Cys Ala
            115                 120                 125
Val Lys Gly Tyr Lys Cys Ile Ile Val Met Pro Glu Lys Met Ser Asn
            130                 135             140
Glu Lys Val Ser Ala Leu Arg Thr Leu Gly Ala Lys Ile Ile Arg Thr
145                 150                 155                 160
Pro Thr Glu Ala Ala Tyr Asp Ser Pro Glu Gly Leu Ile Tyr Val Ala
                165                 170                 175
Gln Gln Leu Gln Arg Glu Thr Pro Asn Ser Ile Val Leu Asp Gln Tyr
            180                 185                 190
Arg Asn Ala Gly Asn Pro Leu Ala His Tyr Asp Gly Thr Ala Ala Glu
            195                 200                 205
Ile Leu Trp Gln Leu Asp Asn Lys Val Asp Met Ile Val Val Ser Ala
            210                 215                 220
Gly Thr Ala Gly Thr Ile Ser Gly Ile Gly Arg Lys Ile Lys Glu Gln
225                 230                 235                 240
Val Pro Ser Cys Gln Ile Val Gly Val Asp Pro Tyr Gly Ser Ile Leu
                245                 250                 255
Ala Arg Pro Ala Glu Leu Asn Lys Thr Asp Val Gln Phe Tyr Glu Val
            260                 265                 270
Glu Gly Ile Gly Tyr Asp Phe Pro Pro Thr Val Phe Asp Asp Thr Val
            275                 280                 285
Val Asp Val Trp Thr Lys Ile Gly Asp Ser Asp Cys Phe Pro Met Ser
            290                 295             300
Arg Arg Leu Asn Ala Glu Glu Gly Leu Leu Cys Gly Gly Ser Ser Gly
305                 310                 315                 320
Gly Ala Met His Ala Ala Leu Glu His Ala Arg Lys Leu Lys Lys Gly
                325                 330                 335
Gln Arg Cys Val Val Ile Leu Pro Asp Gly Ile Arg Asn Tyr Met Thr
            340                 345                 350
Lys Phe Val Ser Asp Asn Trp Met Glu Ala Arg Asn Phe Lys Glu Pro
            355                 360                 365
Val Asn Glu His Gly His Trp Trp Trp Ser Leu Ala Ile Ala Glu Leu
            370                 375             380
Glu Leu Pro Ala Pro Val Ile Leu Lys Ser Asp Ala Thr Val Gly
385                 390                 395                 400
Glu Ala Ile Ala Leu Met Lys Lys His Arg Val Asp Gln Leu Pro Val
                405                 410                 415
Val Asp Gln Asp Asp Gly Ser Val Leu Gly Val Val Gly Gln Glu Thr
            420                 425                 430
Leu Ile Thr Gln Ile Val Ser Met Asn Arg Gln Gln Ser Asp Pro Ala
            435                 440                 445
Ile Lys Ala Leu Asn Lys Arg Val Ile Arg Leu Asn Glu Ser Glu Ile
            450                 455             460
Leu Gly Lys Leu Ala Arg Val Leu Glu Val Asp Pro Ser Val Leu Ile
465                 470                 475                 480
Leu Gly Lys Asn Pro Ala Gly Lys Val Glu Leu Lys Ala Leu Ala Thr
                485                 490                 495
Lys Leu Asp Val Thr Thr Phe Ile Ala Ala Gly Lys Gln Lys Pro Lys
            500                 505                 510
Ala Asn Gly Thr Thr Asn Gly Gly Ser His
            515                 520
```

<210> SEQ ID NO 19
<211> LENGTH: 497
<212> TYPE: PRT
<213> ORGANISM: Dictyostelium discoideum

<400> SEQUENCE: 19

```
Met Ser Ala Pro Glu Gly Pro Ser Lys Cys Thr Trp Thr Pro Asn Thr
1               5                   10                  15

Thr Glu Asn Thr Pro His Thr Thr Arg Arg Thr Pro Lys Lys Leu Ile
            20                  25                  30

Met Asp Asn Ile Leu Asp Asn Ile Gly Gly Thr Pro Leu Val Arg Val
        35                  40                  45

Asn Lys Val Ser Ser Asp Leu Glu Cys Glu Leu Val Ala Lys Cys Glu
50                  55                  60

Phe Phe Asn Ala Gly Gly Ser Val Lys Asp Arg Ile Gly His Arg Met
65                  70                  75                  80

Ile Val Asp Ala Glu Ser Gly Arg Ile Lys Lys Gly Asp Thr Leu
            85                  90                  95

Ile Glu Pro Thr Ser Gly Asn Thr Gly Ile Gly Leu Ala Leu Thr Ala
            100                 105                 110

Ala Ile Lys Gly Tyr Lys Met Ile Ile Thr Leu Pro Glu Lys Met Ser
        115                 120                 125

Gln Glu Lys Val Asp Val Leu Lys Ala Leu Gly Gly Glu Ile Ile Arg
130                 135                 140

Thr Pro Thr Glu Ala Ala Phe Asp Ala Pro Glu Ser His Ile Gly Val
145                 150                 155                 160

Ala Lys Lys Leu Asn Ser Glu Ile Pro Asn Ser His Ile Leu Asp Gln
            165                 170                 175

Tyr Gly Asn Pro Ser Asn Pro Leu Ala His Tyr Asp Gly Thr Ala Glu
        180                 185                 190

Glu Leu Leu Glu Gln Cys Glu Gly Lys Ile Asp Met Ile Val Cys Thr
        195                 200                 205

Ala Gly Thr Gly Gly Thr Ile Thr Gly Ile Ala Arg Lys Ile Lys Glu
210                 215                 220

Arg Leu Pro Asn Cys Ile Val Val Gly Val Asp Pro His Gly Ser Ile
225                 230                 235                 240

Leu Ala Gln Pro Glu Ser Leu Asn Asn Thr Asn Lys Ser Tyr Lys Ile
            245                 250                 255

Glu Gly Ile Gly Tyr Asp Phe Ile Pro Asn Val Leu Glu Arg Lys Leu
        260                 265                 270

Val Asp Gln Trp Ile Lys Thr Asp Lys Glu Ser Phe Ile Met Ala
        275                 280                 285

Arg Arg Leu Ile Lys Glu Glu Gly Leu Leu Cys Ala Gly Ser Ser Gly
290                 295                 300

Ser Ala Met Val Gly Ala Leu Leu Ala Ala Lys Gln Leu Lys Lys Gly
305                 310                 315                 320

Gln Arg Cys Val Val Leu Leu Ala Asp Ser Ile Arg Asn Tyr Met Thr
            325                 330                 335

Lys His Leu Asn Asp Asp Trp Leu Val Asp Asn Gly Phe Val Asp Pro
        340                 345                 350

Glu Tyr Lys Thr Lys Asp Gln Gln Glu Glu Glu Lys Tyr His Gly Ala
        355                 360                 365

Thr Val Lys Asp Leu Thr Leu Pro Lys Pro Ile Thr Ile Ser Ala Thr
```

```
                370                 375                 380
Thr Thr Cys Ala Ala Ala Val Gln Leu Leu Gln Gln Tyr Gly Phe Asp
385                 390                 395                 400

Gln Leu Pro Val Val Ser Glu Ser Lys Lys Val Leu Val Asn Ser Leu
                405                 410                 415

Leu Val Thr Ser Leu Thr Tyr Ala Ser Lys Lys Ala Val Pro Thr Asp
                420                 425                 430

Ala Val Ser Lys Val Met Phe Arg Phe Thr Lys Asn Glu Lys Tyr Ile
                435                 440                 445

Pro Ile Thr Gln Ser Thr Ser Leu Ala Thr Leu Ser Lys Phe Phe Glu
                450                 455                 460

Asn His Ser Ser Ala Ile Val Thr Glu Asn Asp Glu Ile Ile Ser Ile
465                 470                 475                 480

Val Thr Lys Ile Asp Leu Leu Thr Tyr Leu Met Lys Ser Gln Gln Lys
                485                 490                 495

Asn

<210> SEQ ID NO 20
<211> LENGTH: 507
<212> TYPE: PRT
<213> ORGANISM: Saccharomyces cerevisiae

<400> SEQUENCE: 20

Met Thr Lys Ser Glu Gln Gln Ala Asp Ser Arg His Asn Val Ile Asp
1               5                   10                  15

Leu Val Gly Asn Thr Pro Leu Ile Ala Leu Lys Lys Leu Pro Lys Ala
                20                  25                  30

Leu Gly Ile Lys Pro Gln Ile Tyr Ala Lys Leu Glu Leu Tyr Asn Pro
            35                  40                  45

Gly Gly Ser Ile Lys Asp Arg Ile Ala Lys Ser Met Val Glu Glu Ala
        50                  55                  60

Glu Ala Ser Gly Arg Ile His Pro Ser Arg Ser Thr Leu Ile Glu Pro
65                  70                  75                  80

Thr Ser Gly Asn Thr Gly Ile Gly Leu Ala Leu Ile Gly Ala Ile Lys
                85                  90                  95

Gly Tyr Arg Thr Ile Ile Thr Leu Pro Glu Lys Met Ser Asn Glu Lys
            100                 105                 110

Val Ser Val Leu Lys Ala Leu Gly Ala Glu Ile Ile Arg Thr Pro Thr
        115                 120                 125

Ala Ala Ala Trp Asp Ser Pro Glu Ser His Ile Gly Val Ala Lys Lys
    130                 135                 140

Leu Glu Lys Glu Ile Pro Gly Ala Val Ile Leu Asp Gln Tyr Asn Asn
145                 150                 155                 160

Met Met Asn Pro Glu Ala His Tyr Phe Gly Thr Gly Arg Glu Ile Gln
                165                 170                 175

Arg Gln Leu Glu Asp Leu Asn Leu Phe Asp Asn Leu Arg Ala Val Val
            180                 185                 190

Ala Gly Ala Gly Thr Gly Gly Thr Ile Ser Gly Ile Ser Lys Tyr Leu
        195                 200                 205

Lys Glu Gln Asn Asp Lys Ile Gln Ile Val Gly Ala Asp Pro Phe Gly
    210                 215                 220

Ser Ile Leu Ala Gln Pro Glu Asn Leu Asn Lys Thr Asp Ile Thr Asp
225                 230                 235                 240

Tyr Lys Val Glu Gly Ile Gly Tyr Asp Phe Val Pro Gln Val Leu Asp
```

```
            245                 250                 255
Arg Lys Leu Ile Asp Val Trp Tyr Lys Thr Asp Asp Lys Pro Ser Phe
        260                 265                 270

Lys Tyr Ala Arg Gln Leu Ile Ser Asn Glu Gly Val Leu Val Gly Gly
    275                 280                 285

Ser Ser Gly Ser Ala Phe Thr Ala Val Val Lys Tyr Cys Glu Asp His
290                 295                 300

Pro Glu Leu Thr Glu Asp Val Ile Val Ala Ile Phe Pro Asp Ser
305                 310                 315                 320

Ile Arg Ser Tyr Leu Thr Lys Phe Val Asp Asp Glu Trp Leu Lys Lys
                325                 330                 335

Asn Asn Leu Trp Asp Asp Val Leu Ala Arg Phe Asp Ser Ser Lys
                340                 345                 350

Leu Glu Ala Ser Thr Thr Lys Tyr Ala Asp Val Phe Gly Asn Ala Thr
            355                 360                 365

Val Lys Asp Leu His Leu Lys Pro Val Val Ser Val Lys Glu Thr Ala
370                 375                 380

Lys Val Thr Asp Val Ile Lys Ile Leu Lys Asp Asn Gly Phe Asp Gln
385                 390                 395                 400

Leu Pro Val Leu Thr Glu Asp Gly Lys Leu Ser Gly Leu Val Thr Leu
                405                 410                 415

Ser Glu Leu Leu Arg Lys Leu Ser Ile Asn Asn Ser Asn Asn Asp Asn
            420                 425                 430

Thr Ile Lys Gly Lys Tyr Leu Asp Phe Lys Lys Leu Asn Asn Phe Asn
435                 440                 445

Asp Val Ser Ser Tyr Asn Glu Asn Lys Ser Gly Lys Lys Phe Ile
    450                 455                 460

Lys Phe Asp Glu Asn Ser Lys Leu Ser Asp Leu Asn Arg Phe Phe Glu
465                 470                 475                 480

Lys Asn Ser Ser Ala Val Ile Thr Asp Gly Leu Lys Pro Ile His Ile
                485                 490                 495

Val Thr Lys Met Asp Leu Leu Ser Tyr Leu Ala
            500                 505

<210> SEQ ID NO 21
<211> LENGTH: 325
<212> TYPE: PRT
<213> ORGANISM: Triticum aestivum

<400> SEQUENCE: 21

Met Gly Glu Ala Ser Ser Pro Ala Ile Ala Lys Asp Val Thr Glu Leu
1               5                   10                  15

Ile Gly Asn Thr Pro Leu Val Tyr Leu Asn Lys Val Thr Asp Gly Cys
                20                  25                  30

Val Gly Arg Val Ala Ala Lys Leu Glu Ser Met Glu Pro Cys Ser Ser
            35                  40                  45

Val Lys Asp Arg Ile Gly Tyr Ser Met Ile Thr Asp Ala Glu Glu Lys
        50                  55                  60

Gly Phe Ile Val Pro Gly Lys Ser Val Leu Ile Glu Pro Thr Ser Gly
65                  70                  75                  80

Asn Thr Gly Ile Gly Leu Ala Phe Met Ala Ala Lys Gly Tyr Arg
                85                  90                  95

Leu Val Leu Thr Met Pro Ala Ser Met Ser Met Glu Arg Arg Ile Ile
                100                 105                 110
```

```
Leu Lys Ala Phe Gly Ala Glu Leu Ile Leu Thr Asp Pro Leu Leu Gly
            115                 120                 125

Met Lys Gly Ala Val Gln Lys Ala Glu Leu Ala Ala Lys Thr Pro
    130                 135                 140

Asn Ser Tyr Ile Leu Gln Gln Phe Glu Asn Ala Ala Asn Pro Lys Ile
145                 150                 155                 160

His Tyr Glu Thr Thr Gly Pro Glu Ile Trp Lys Gly Thr Gly Gly Lys
                165                 170                 175

Ile Asp Gly Leu Val Ser Gly Ile Gly Thr Gly Gly Thr Ile Thr Gly
                180                 185                 190

Thr Gly Lys Tyr Leu Gln Glu Gln Asn Pro Asn Ile Lys Leu Tyr Gly
            195                 200                 205

Val Glu Pro Thr Glu Ser Ala Ile Leu Asn Gly Gly Lys Pro Gly Pro
210                 215                 220

His Lys Ile Gln Gly Ile Gly Ala Gly Phe Ile Pro Gly Val Leu Asp
225                 230                 235                 240

Val Asp Ile Ile Asp Glu Thr Ile Gln Val Ser Ser Asp Glu Ser Ile
                245                 250                 255

Glu Met Ala Lys Ser Leu Ala Leu Lys Glu Gly Leu Leu Val Gly Ile
            260                 265                 270

Ser Ser Gly Ala Ala Ala Ala Ala Ile Lys Val Ala Gln Arg Pro
275                 280                 285

Glu Asn Ala Gly Lys Leu Phe Val Val Val Phe Pro Ser Phe Gly Glu
    290                 295                 300

Arg Tyr Leu Ser Ser Val Leu Phe His Ser Ile Lys Lys Glu Ala Glu
305                 310                 315                 320

Ser Met Val Val Glu
            325

<210> SEQ ID NO 22
<211> LENGTH: 323
<212> TYPE: PRT
<213> ORGANISM: Salmonella typhimurium

<400> SEQUENCE: 22

Met Ser Lys Ile Tyr Glu Asp Asn Ser Leu Thr Ile Gly His Thr Pro
1               5                   10                  15

Leu Val Arg Leu Asn Arg Ile Gly Asn Gly Arg Ile Leu Ala Lys Val
                20                  25                  30

Glu Ser Arg Asn Pro Ser Phe Ser Val Lys Cys Arg Ile Gly Ala Asn
            35                  40                  45

Met Ile Trp Asp Ala Glu Lys Arg Gly Val Leu Lys Pro Gly Val Glu
50                  55                  60

Leu Val Glu Pro Thr Ser Gly Asn Thr Gly Ile Ala Leu Ala Tyr Val
65                  70                  75                  80

Ala Ala Ala Arg Gly Tyr Lys Leu Thr Leu Thr Met Pro Glu Thr Met
                85                  90                  95

Ser Ile Glu Arg Arg Lys Leu Leu Lys Ala Leu Gly Ala Asn Leu Val
            100                 105                 110

Leu Thr Glu Gly Ala Lys Gly Met Lys Gly Ala Ile Gln Lys Ala Glu
        115                 120                 125

Glu Ile Val Ala Ser Asp Pro Gln Lys Tyr Leu Leu Leu Gln Gln Phe
    130                 135                 140

Ser Asn Pro Ala Asn Pro Glu Ile His Glu Lys Thr Thr Gly Pro Glu
145                 150                 155                 160
```

```
Ile Trp Glu Asp Thr Asp Gly Gln Val Asp Val Phe Ile Ser Gly Val
            165                 170                 175

Gly Thr Gly Gly Thr Leu Thr Gly Val Thr Arg Tyr Ile Lys Gly Thr
            180                 185                 190

Lys Gly Lys Thr Asp Leu Ile Thr Val Ala Val Glu Pro Thr Asp Ser
            195                 200                 205

Pro Val Ile Ala Gln Ala Leu Ala Gly Glu Glu Ile Lys Pro Gly Pro
        210                 215                 220

His Lys Ile Gln Gly Ile Gly Ala Gly Phe Ile Pro Gly Asn Leu Asp
225                     230                 235                 240

Leu Lys Leu Ile Asp Lys Val Val Gly Ile Thr Asn Glu Glu Ala Ile
                245                 250                 255

Ser Thr Ala Arg Arg Leu Met Glu Glu Glu Gly Ile Leu Ala Gly Ile
            260                 265                 270

Ser Ser Gly Ala Ala Val Ala Ala Ala Leu Lys Leu Gln Glu Asp Glu
        275                 280                 285

Ser Phe Thr Asn Lys Asn Ile Val Val Ile Leu Pro Ser Ser Gly Glu
        290                 295                 300

Arg Tyr Leu Ser Thr Ala Leu Phe Ala Asp Leu Phe Thr Glu Lys Glu
305                 310                 315                 320

Leu Gln Gln
```